(12) United States Patent
Cicic

(10) Patent No.: US 11,364,235 B2
(45) Date of Patent: Jun. 21, 2022

(54) METHOD FOR TREATING CANCER USING A BCL-2 INHIBITOR IN CONJUNCTION WITH AN ALPHA-EMITTING RADIOIMMUNOTHERAPEUTIC

(71) Applicant: Actinium Pharmaceuticals, Inc., New York, NY (US)

(72) Inventor: Dragan Cicic, Brooklyn, NY (US)

(73) Assignee: Actinium Pharmaceuticals, Inc., New York, NY (US)

( * ) Notice: Subject to any disclaimer, the term of this patent is extended or adjusted under 35 U.S.C. 154(b) by 319 days.

(21) Appl. No.: 16/607,168

(22) PCT Filed: Apr. 26, 2018

(86) PCT No.: PCT/US2018/029607
§ 371 (c)(1),
(2) Date: Oct. 22, 2019

(87) PCT Pub. No.: WO2018/200841
PCT Pub. Date: Nov. 1, 2018

(65) Prior Publication Data
US 2020/0383974 A1   Dec. 10, 2020

Related U.S. Application Data

(60) Provisional application No. 62/491,803, filed on Apr. 28, 2017.

(51) Int. Cl.
| | | |
|---|---|---|
| A61K 31/496 | (2006.01) | |
| A61P 35/02 | (2006.01) | |
| A61K 51/10 | (2006.01) | |
| C07K 16/28 | (2006.01) | |

(52) U.S. Cl.
CPC ........ *A61K 31/496* (2013.01); *A61K 51/1069* (2013.01); *A61P 35/02* (2018.01); *C07K 16/2803* (2013.01)

(58) Field of Classification Search
CPC .................................................. A61K 31/496
See application file for complete search history.

(56) References Cited

U.S. PATENT DOCUMENTS

| | | |
|---|---|---|
| 8,546,399 B2 | 10/2013 | Bruncko et al. |
| 2016/0096892 A1* | 4/2016 | Brogdon .......... A61K 39/39558 424/93.21 |
| 2016/0362472 A1 | 12/2016 | Bitter et al. |

FOREIGN PATENT DOCUMENTS

WO   WO2016044605   3/2016

OTHER PUBLICATIONS

McMahon et al. (2000).*
Pinedo et al. (2000).*
Bourke et al., Correlation of Radiation Response with Tumor Oxygenation in the Dunning Prostate R3327-AT1 Tumor. Int. J. Radiat. Oncol. Biol. Phys. Mar. 15, 2007; 67(4):1179-1186.
FDA News Release, FDA approves new drug for chronic lymphocytic leukemia in patients with a specific chromosomal abnormality, Apr. 11, 2016.
Friesen, et al., Breaking Chemoresistance and Radioresistance with [$^{213}$Bi]anti-CD45 Antibodies in Leukemia Cells, Cancer Res 2007, 67(5):1950-8.
Fulda, Tumor resistance to apoptosis, Int. J. Cancer, 2009, 124:511-515.
Garg et al. 225Ac-labeled CD33-targeting antibody reverses resistance to Bcl-2 inhibitor venetoclax in acute myeloid leukemia models. Cancer Medicine, 2021, 10:1128-1140.
Graf et al., (2014), DNA Double Strand Breaks as Predictor of Efficacy of the Alpha-Particle Emitter Ac-225 and the Electron Emitter Lu-177 for Somatostatin Receptor Targeted Radiotherapy. PLoS ONE 9(2): e88239. doi:10.1371/journal.pone.0088239.
Hamada et al., The small-molecule Bcl-2 inhibitor HA14-1 sensitizes cervical cancer cells, but not normal fibroblasts, to heavy-ion radiation, Radiotherapy and Oncology, 2008, vol. 89, No. 2, pp. 227-230.
Hara et al., Bcl-2 inhibitors potentiate the cytotoxic effects of radiation in Bcl-2 overexpressing radioresistant tumor cells, International Journal of Radiation: Oncology Biology Physics, 2005, vol. 61, No. 2, pp. 517-528.
Harrison et al., Hypoxia and Anemia: Factors in Decreased Sensitivity to Radiation Therapy and Chemotherapy? The Oncologist 2004, 9 (Suppl. 5), 31-40.
Hockel et al., Tumor Hypoxia: Definitions and Current Clinical, Biologic, and Molecular Aspects, Journal of the National Cancer Institute, vol. 93, No. 4, Feb. 21, 2001, p. 266-276.
Jeggo et al., DNA double-strand breaks: their cellular and clinical impact? Oncogene (2007) 26, 7717-7719.

(Continued)

*Primary Examiner* — Paul V Ward
(74) *Attorney, Agent, or Firm* — Paul Diamond, Esq.

(57) ABSTRACT

This invention provides a method for treating a subject afflicted with cancer, comprising administering to the subject (i) a BCL-2 inhibitor in conjunction with (ii) an alpha-emitting isotope-labeled agent that targets cancer cells in the subject, wherein the amounts of the BCL-2 inhibitor and labeled agent, when administered in conjunction with one another, are therapeutically effective. This invention also provides a method for inducing the death of a cancer cell, comprising contacting the cell with (i) a BCL-2 inhibitor in conjunction with (ii) an alpha-emitting isotope-labeled agent that targets the cancer cell, wherein the amounts of BCL-2 inhibitor and labeled agent, when concurrently contacted with the cell, are effective to induce the cell's death.

18 Claims, 10 Drawing Sheets
Specification includes a Sequence Listing.

(56) References Cited

OTHER PUBLICATIONS

Jurcic et al., Phase I Trial of Targeted Alpha-Particle Therapy with Actinium-225 (225Ac)-Lintuzumab and Low-Dose Cytarabine (LDAC) in Patients Age 60 or Older with Untreated Acute Myeloid Leukemia (AML). Blood, Dec. 2016, 128(22): 4050.
Jurcic et al., Targeted α Particle immunotherapy for Myeloid Leukemia, Blood, 2002, vol. 100, No. 4, pp. 1233-1239.
Kiang et al., Radiation Combined Injury: DNA Damage, Apoptosis, and Autophagy. Adaptive Medicine 2(1): 1-10, 2010.
Konishi et al., Involvement of Histone H1.2 in Apoptosis Induced by DNA Double-Strand Breaks. Cell, Sep. 19, 2003, vol. 114, 673-688.
Kroemer et al., Classification of Cell Death: Recommendations of the Nomenclature Committee on Cell Death 2009. Cell Death and Differentiation, 2009, 16, 3-11.
Miederer et al., Pharmacokinetics, Dosimetry, and Toxicity of the Targetable Atomic Generator, 225Ac-HuM195, in Nonhuman Primates, Journal of Nuclear Medicine, 2004, vol. 45, No. 1, pp. 129-137.
Moretti et al., AT-101, a Pan-Bcl-2 Inhibitor, Leads to Radiosensitization of Non-small Cell Lung Cancer, Journal of Thoracic Oncology, US, 2010, vol. 5, No. 5, doi:10.1097/JTO.0b013e3181d6e08e, ISSN 1556-0864, pp. 680-687.
O'Steen et al., Venetoclax Synergizes with Radiation Therapy for Treatment of B-Cell Lymphomas. Blood, 2016, 128 (22):467.
O'Steen et al., Venetoclax Synergizes with Radiation Therapy for Treatment of B-Cell Lymphomas. Cancer Res 2017,77:3885-3893.
Pogozelski et al., Quantitative assessment of the contribution of clustered damage to DNA double-strand breaks induced by 60Co gamma rays and fission neutrons. Radiat. Res. Apr. 1999, 151(4):442-8.
Potter et al., To Prime, or Not to Prime: That Is the Question, Cold Spring Harbor Symposia on Quantitative Biology, vol. LXXXI, Nov. 3, 2016, pp. 131-140.
Pullarkat et al., BCL2 Inhibition by Venetoclax: Targeting the Achilles' Heel of the Acute Myeloid Leukemia Stem Cell?, Cancer Discovery, Oct. 2016, 6, pp. 1082-1083.
Rizvi et al., In vitro testing of the leukaemia monoclonal antibody WM-53 labeled with alpha and beta emitting radioisotopes, Leukemia Research, US, 2002, vol. 26, No. 1, pp. 37-43.
Roscher et al., Targeted alpha-therapy using [Bi-213]anti-CD20 as novel treatment option for radio-and chemoresistant non-Hodgkin lymphoma cells, Oncotarget, Feb. 2013, vol. 4, No. 2, pp. 218-230.
Shiozaki, et al., Mechanism of XIAP-Mediated Inhibition of Caspase-9. Molecular Cell, Feb. 2003, vol. 11, pp. 519-552.
Sofou, Radionuclide carriers for targeting of cancer, International Journal of Nanomedicine 2008:3(2), pp. 181-199.
Stap et al., Induction of linear tracks of DNA double-strand breaks by alpha-particle irradiation of cells. Nat. Methods, Mar. 2008, 5(3):261-6.
Tamm et al., Expression and prognostic significance of IAP-family genes in human cancers and myeloid leukemias. Clin Cancer Res. 2000; 6(5):1796-1803.
U.S. Food and Drug Administration., Prescribing Information for VENCLEXTA™, issued Apr. 2016, <https://www.accessdata.fda.gov/drugsatfda_docs/label/2016/208573s000lbl.pdf [retrieved Sep. 28, 2021 (Sep. 28, 2021]>.
Vaupel, Tumor microenvironmental physiology and its implications for radiation oncology. Seminars in Radiation Oncology, Jul. 2004, vol. 14, Issue 3, pp. 198-206.
Venetoclax Advisory Committee Briefing Document, Jun. 28, 2016.
Widden et al., The multiple mechanisms of MCL1 in the regulation of cell fate. Communications Biology, 2021, 4:1029, pp. 1-12.
Wilder et al., International Prognostic Index-Based Outcomes for Diffuse Large B-Cell Lymphomas. Cancer Jun. 15, 2002, vol. 94, No. 12, pp. 3083-3088.
Zevalin® U.S.A. Package Insert (2001).
International Preliminary Report on Patentability dated Oct. 29, 2019 in International App. No. PCT/US18/29607, CICIC, Dragan, Actinium Pharmaceuticals Inc.
International Search Report dated Sep. 10, 2018 in International App. No. PCT/US18/29607, CICIC, Dragan, Actinium Pharmaceuticals Inc.

* cited by examiner

```
 624 TCTAGACCACCATGGAGAAAGACACACTCCTGCTATGGGTCCTACTTCTCTGGGTTCCAGGTTCCACAGGTGACATTCAG
      M  E  K  D  T  L  L  L  W  V  L  L  L  W  V  P  G  S  T  G  D  I  Q
 704 ATGACCCAGTCTCCGAGCTCTCTGTCCGCATCAGTAGGAGACAGGGTCACCATCACATGCAGAGCCAGCGAAAGTGTCGA
          M  T  Q  S  P  S  S  L  S  A  S  V  G  D  R  V  T  I  T  C  R  A  S  E  S  V  D
 784 CAATTATGGCATTAGCTTTATGAACTGGTTCCAACAGAAACCCGGGAAGGCTCCTAAGCTTCTGATTTACGCTGCATCCA
        N  Y  G  I  S  F  M  N  W  F  Q  Q  K  P  G  K  A  P  K  L  L  I  Y  A  A  S
 864 ACCAAGGCTCCGGGGTACCCTCTCGCTTCTCAGGCAGTGGATCTGGGACAGACTTCACTCTCACCATTTCATCTCTGCAG
        N  Q  G  S  G  V  P  S  R  F  S  G  S  G  S  G  T  D  F  T  L  T  I  S  S  L  Q
 944 CCTGATGACTTCGCAACCTATTACTGTCAGCAAAGTAAGGAGGTTCCGTGGACGTTCGGTCAAGGGACCAAGGTGGAGAT
        P  D  D  F  A  T  Y  Y  C  Q  Q  S  K  E  V  P  W  T  F  G  Q  G  T  K  V  E  I
1024 CAAACGTAAGTAGAATCCAAAGTCTAGAAATTCTAAACTCTGAGGGGGTCGGATGACGTGGCCATTCTTTGCCTAAAGCA
        K  R
1104 TTGAGTTTACTGCAAGGTCAGAAAAGCATGCAAAGCCCTCAGAATGGCTGCAAAGAGCTCCAACAAAACAATTTAGAACT

1184 TTATTAAGGAATAGGGGGAAGCTAGGAAGAAACTCAAAACATCAAGATTTTAAATACGCTTCTTGGTCTCCTTGCTATAA

1264 TTATCTGGGATAAGCATGCTGTTTTCTGTCTGTCCCTAACATGCTCTGTGATTATCCGCAAACAACACACCCAAGGGCAG

1344 AACTTTGTTACTTAAACACCATCCTGTTTGCTTCTTTCCTCAGGAACTGTGGCTGCACCATCTGTCTTCATCTTCCCGCC
                                                                T  V  A  A  P  S  V  F  I  F  P  P
1424 ATCTGATGAGCAGTTGAAATCTGGAACTGCCTCTGTTGTGTGCCTGCTGAATAACTTCTATCCCAGAGAGGCCAAAGTAC
        S  D  E  Q  L  K  S  G  T  A  S  V  V  C  L  L  N  N  F  Y  P  R  E  A  K  V
1504 AGTGGAAGGTGGATAACGCCCTCCAATCGGGTAACTCCCAGGAGAGTGTCACAGAGCAGGACAGCAAGGACAGCACCTAC
        Q  W  K  V  D  N  A  L  Q  S  G  N  S  Q  E  S  V  T  E  Q  D  S  K  D  S  T  Y
1584 AGCCTCAGCAGCACCCTGACGCTGAGCAAAGCAGACTACGAGAAACACAAAGTCTACGCCTGCGAAGTCACCCATCAGGG
        S  L  S  S  T  L  T  L  S  K  A  D  Y  E  K  H  K  V  Y  A  C  E  V  T  H  Q  G
1664 CCTGAGCTCGCCCGTCACAAAGAGCTTCAACAGGGGAGAGTGTTAGAGGGAGAAGTGCCCCCACCTGCTCCTCAGTTCCA
        L  S  S  P  V  T  K  S  F  N  R  G  E  C
1744 GCCTGACCCCCTCCCATCCTTTGGCCTCTGACCCTTTTTCCACAGGGGACCTACCCCTATTGCGGTCCTCCAGCTCATCT

1824 TTCACCTCACCCCCTCCTCCTCCTTGGCTTTAATTATGCTAATGTTGGAGGAGAATGAATAAATAAAGTGAATCTTTGC

1904 ACCTGTGGTTTCTCTCTTTCCTCATTTAATAATTATTATCTGTTGTTTTACCAACTACTCAATTTCTCTTATAAGGGACT

1984 AAATATGTAGTCATCCTAAGGCGCATAACCATTTATAAAAATCATCCTTCATTCTATTTTACCCTATCATCCTCTGCAAG

2064 ACAGTCCTCCCTCAAACCCACAAGCCTTCTGTCCTCACAGTCCCTGGGCCATGGTAGGAGAGACTTGCTTCCTTGTTTT

2144 CCCCTCCTCAGCAAGCCCTCATAGTCCTTTTTAAGGGTGACAGGTCTTACAGTCATATATCCTTTGATTCAATTCCCTGA

2224 GAATCAACCAAAGCAAATTTTTCAAAAGAAGAAACCTGCTATAAAGAGAATCATTCATTGCAACATGATATAAAATAACA

2304 ACACAATAAAAGCAATTAAATAAACAAACAATAGGGAAATGTTTAAGTTCATCATGGTACTTAGACTTAATGGAATGTCA

2384 TGCCTTATTTACATTTTTAAACAGGTACTGAGGGACTCCTGTCTGCCAAGGGCCGTATTGAGTACTTTCCACAACCTAAT

2464 TTAATCCACACTATACTGTGAGATTAAAAACATTCATTAAAATGTTGCAAAGGTTCTATAAAGCTGAGAGACAAATATAT

2544 TCTATAACTCAGCAATCCCACTTCTAGGATCC
```

Figure 2

```
 624 TCTAGACCACCATGGGATGGAGCTGGATCTTTCTCTTCCTCCTGTCAGGAACTGCTGGCGTCCACTCTCAGGTTCAGCTG
                M  G  W  S  W  I  F  L  F  L  L  S  G  T  A  G  V  H  S  Q  V  Q  L
 704 GTGCAGTCTGGAGCTGAGGTGAAGAAGCCTGGGAGCTCAGTGAAGGTTTCTGCAAAGCTTCTGGCTACACCTTCACTGA
      V  Q  S  G  A  E  V  K  K  P  G  S  S  V  K  V  S  C  K  A  S  G  Y  T  F  T  D
 784 CTACAACATGCACTGGGTGAGGCAGGCTCCTGGCCAAGGCCTGGAATGGATTGGATATATTTATCCTTACAATGGTGGTA
       Y  N  M  H  W  V  R  Q  A  P  G  Q  G  L  E  W  I  G  Y  I  Y  P  Y  N  G  G
 864 CCGGCTACAACCAGAAGTTCAAGAGCAAGGCCACAATTACAGCAGACGAGAGTACTAACACAGCCTACATGGAACTCTCC
      T  G  Y  N  Q  K  F  K  S  K  A  T  I  T  A  D  E  S  T  N  T  A  Y  M  E  L  S
 944 AGCCTGAGGTCTGAGGACACTGCAGTCTATTACTGCGCAAGAGGGCGCCCCGCTATGGACTACTGGGCCAAGGGACTCT
       S  L  R  S  E  D  T  A  V  Y  Y  C  A  R  G  R  P  A  M  D  Y  W  G  Q  G  T  L
1024 GGTCACTGTCTCTTCAGGTAAGAATGGCCTCTAGACCACCATGGGATGGAGCTTTCTGGGCAGGCCAGGCCTGACCTTG
       V  T  V  S  S
1104 GCTTTGGGGCAGGGACGGGGCTAAGGTGAGGCAGGTGGCGCCAGCCAGGTGCACACCCAATGCCCATGAGCCCAGACACT

1184 GGACGCTGAACCTCGCGGACAGTTAAGAACCCAGGGGCCTCTGCGCCCTGGGCCCAGCTCTGTCCCACACCGCGGTCACA

1264 TGGCACCACCTCTCTTGCAGCCTCCACCAAGGGCCCATCGGTCTTCCCCCTGGCACCCTCCTCCAAGAGCACCTCTGGGG
                        A  S  T  K  G  P  S  V  F  P  L  A  P  S  S  K  S  T  S  G
1344 GCACAGCGGCCCTGGGCTGCCTGGTCAAGGACTACTTCCCCGAACCGGTGACGGTGTCGTGGAACTCAGGCGCCCTGACC
       G  T  A  A  L  G  C  L  V  K  D  Y  F  P  E  P  V  T  V  S  W  N  S  G  A  L  T
1424 AGCGGCGTGCACACCTTCCCGGCTGTCCTACAGTCCTCAGGACTCTACTCCCTCAGCAGCGTGGTGACCGTGCCCTCCAG
       S  G  V  H  T  F  P  A  V  L  Q  S  S  G  L  Y  S  L  S  S  V  V  T  V  P  S  S
1504 CAGCTTGGGCACCCAGACCTACATCTGCAACGTGAATCACAAGCCCAGCAACACCAAGGTGGACAAGAAAGTTGGTGAGA
       S  L  G  T  Q  T  Y  I  C  N  V  N  H  K  P  S  N  T  K  V  D  K  K  V
1584 GGCCAGCACAGGGAGGGAGGGTGTCTGCTGGAAGCCAGGCTCAGCGCTCCTGCCTGGACGCATCCCGGCTATGCAGCCCC

1664 AGTCCAGGGCAGCAAGGCAGGCCCCGTCTGCCTCTTCACCCGGAGGCCTCTGCCCGCCCCACTCATGCTCAGGGAGAGGG

1744 TCTTCTGGCTTTTTCCCCAGGCTCTGGGCAGGCACAGGCTAGGTGCCCCTAACCCAGGCCCTGCACACAAAGGGGCAGGT

1824 GCTGGGCTCAGACCTGCCAAGAGCCATATCCGGGAGGACCCTGCCCCTGACCTAAGCCCACCCCAAAGGCCAAACTCTCC

1904 ACTCCCTCAGCTCGGACACCTTCTCTCCTCCCAGATTCCAGTAACTCCCAATCTTCTCTCTGCAGAGCCCAAATCTTGTG
                                                                        E  P  K  S  C
1984 ACAAAACTCACACATGCCCACCGTGCCCAGGTAAGCCAGCCCAGGCCTCGCCCTCCAGCTCAAGGCGGGACAGGTGCCCT
       D  K  T  H  T  C  P  P  C  P
2064 AGAGTAGCCTGCATCCAGGGACAGGCCCCAGCCGGGTGCTGACACGTCCACCTCCATCTCTTCCTCAGCACCTGAACTCC
                                                                              A  P  E  L
2144 TGGGGGGACCGTCAGTCTTCCTCTTCCCCCCAAAACCCAAGGACACCCTCATGATCTCCCGGACCCCTGAGGTCACATGC
       L  G  G  P  S  V  F  L  F  P  P  K  P  K  D  T  L  M  I  S  R  T  P  E  V  T  C
2224 GTGGTGGTGGACGTGAGCCACGAAGACCCTGAGGTCAAGTTCAACTGGTACGTGGACGGCGTGGAGGTGCATAATGCCAA
       V  V  V  D  V  S  H  E  D  P  E  V  K  F  N  W  Y  V  D  G  V  E  V  H  N  A  K
2304 GACAAAGCCGCGGGAGGAGCAGTACAACAGCACGTACCGTGTGGTCAGCGTCCTCACCGTCCTGCACCAGGACTGGCTGA
       T  K  P  R  E  E  Q  Y  N  S  T  Y  R  V  V  S  V  L  T  V  L  H  Q  D  W  L
2384 ATGGCAAGGAGTACAAGTGCAAGGTCTCCAACAAAGCCCTCCCAGCCCCCATCGAGAAAACCATCTCCAAAGCCAAAGGT
       N  G  K  E  Y  K  C  K  V  S  N  K  A  L  P  A  P  I  E  K  T  I  S  K  A  K
2464 GGGACCCGTGGGGTGCGAGGGCCACATGGACAGAGGCCGGCTCGGCCCACCCTCTGCCCTGAGAGTGACCGCTGTACCAA
```

Figure 3

```
2544 CCTCTGTCCCTACAGGGCAGCCCCGAGAACCACAGGTGTACACCCTGCCCCCATCCCGGGATGAGCTGACCAAGAACCAG
         G  Q  P  R  E  P  Q  V  Y  T  L  P  P  S  R  D  E  L  T  K  N  Q
2624 GTCAGCCTGACCTGCCTGGTCAAAGGCTTCTATCCCAGCGACATCGCCGTGGAGTGGGAGAGCAATGGGCAGCCGGAGAA
      V  S  L  T  C  L  V  K  G  F  Y  P  S  D  I  A  V  E  W  E  S  N  G  Q  P  E  N
2704 CAACTACAAGACCACGCCTCCCGTGCTGGACTCCGACGGCTCCTTCTTCCTCTACAGCAAGCTCACCGTGGACAAGAGCA
        N  Y  K  T  T  P  P  V  L  D  S  D  G  S  F  F  L  Y  S  K  L  T  V  D  K  S
2784 GGTGGCAGCAGGGGAACGTCTTCTCATGCTCCGTGATGCATGAGGCTCTGCACAACCACTACACGCAGAAGAGCCTCTCC
       R  W  Q  Q  G  N  V  F  S  C  S  V  M  H  E  A  L  H  N  H  Y  T  Q  K  S  L  S
2864 CTGTCTCCGGGTAAATGAGTGCGACGGCCGGCAAGCCCCCGCTCCCCGGGCTCTCGCGGTCGCACGAGGATGCTTGGCAC
      L  S  P  G  K
2944 GTACCCCCTGTACATACTTCCCGGGCGCCCAGCATGGAAATAAAGCACCCAGCGCTGCCCTGGGCCCCTGCGAGACTGTG

3024 ATGGTTCTTTCCACGGGTCAGGCCGAGTCTGAGGCCTGAGTGGCATGAGGGAGGCAGAGCGGGTCCCACTGTCCCCACAC

3104 TGGCCCAGGCTGTGCAGGTGTGCCTGGGCCGCCTAGGGTGGGGCTCAGCCAGGGGCTGCCCTCGGCAGGGTGGGGATTT

3184 GCCAGCGTGGCCCTCCCTCCAGCAGCACCTGCCCTGGGCTGGGCCACGGGAAGCCCTAGGAGCCCCTGGGGACAGACACA

3264 CAGCCCCTGCCTCTGTAGGAGACTGTCCTGTTCTGTGAGCGCCCTGTCCTCCGACCTCCATGCCCACTCGGGGGCATGCC

3344 TAGTCCATGTGCGTAGGGACAGGCCCTCCCTCACCCATCTACCCCACGGCACTAACCCCTGGCTGCCCTGCCCAGCCTC

3424 GCACCCGCATGGGGACACAACCGACTCCGGGGACATGCACTCTCGGGCCCTGTGGAGGGACTGGTGCAGATGCCCACACA

3504 CACACTCAGCCCAGACCCGTTCAACAAACCCCGCACTGAGGTTGGCCGGCCACACGGCCACCACACACACGTGCACGC

3584 CTCACACACGGAGCCTCACCCGGGCGAACTGCACAGCACCCAGACCAGAGCAAGGTCCTCGCACACGTGAACACTCCTCG

3664 GACACAGGCCCCACGAGCCCCACGCGGCACCTCAAGGCCCACGAGCCTCTCGGCAGCTTCTCCACATGCTGACCTGCTC

3744 AGACAAACCCAGCCCTCCTCTCACAAGGGTGCCCCTGCAGCCGCCACACACACACAGGGGATCACACACCACGTCACGTC

3824 CCTGGCCCTGGCCCACTTCCCAGTGCCGCCCTTCCCTGCAGGATCC
```

Figure 3 Cont'd

Protocol Schema

Phase I Dose Escalation Component (3+3 Design)

Low Dose Ara-C (LDAC) 20 mg subQ q 12 hrs x 10D Cycle 1

D-1 → D-10

| Fractionated Doses | | LDAC Cycle 2-12 every 28D beginning 4 weeks after dose 2 of Lintuzumab-Ac225 |
|---|---|---|
| Dose 1 | Dose 2 | |
| Lintuzumab-Ac225 | Lintuzumab-Ac225 | |
| D-14-17 | D-18-24 | | plus furosemide and spitonolactone

Phase II Component (Simon 2-stage Design)

Low Dose Ara-C (LDAC) 20 mg subQ q12 hrs X 10D Cycle 1

D-1 → D-10

| Fractionated Doses | | LDAC Cycle 2-12 every 28 D |
|---|---|---|
| Dose 1 | Dose 2 | |
| Lintuzumab-Ac225 | Lintuzumab-Ac225 | |
| D-14-17 | D-18-24 | | plus furosemide and spitonolactone

Dose Escalation Schedule

| Dose Level | Ac-225 Activity per fractionated dose (µCi/Kg) | Total Dose (µCi/Kg) | HuM195 per fractionated dose (µCi/Kg) | Total HuM195 dose (µCi/Kg) |
|---|---|---|---|---|
| 1 | 0.5 | 1.0 | 7.5 | 15 |
| 2 | 1 | 2 | 10 | 20 |
| 3 | 1.5 | 3 | 10 | 20 |
| 4 | 2 | 4 | 12.5 | 25 |

Statistics

Historical CR for this population = 20%

Target CR rate of 35% (p=.05, power = 80%)
Need 7 CRs in first 31 subjects to proceed to stage 2
Total sample size in the Phase II portion = up to 53 subjects Primary endpoint: Response rate (CR + CRp)
Eligibility Patients age ≥ 60 years with newly diagnosed AML with 20% blasts who decline or are considered unfit for intensive induction therapy because of poor risk factors or co-morbid conditions, or subjects ≥ 70 years old with newly diagnosed AML.

Figure 6

| MoA | Beta (low LED) | Alpha (high LED) |
|---|---|---|
| dsDNA breaks (1), (2), (3), (4) | +/- | ++ |
| ssDNA breaks (1), (4) | + | + |
| Direct effect on apoptotic cascade (5), (6) | +/- | ++ |
| Bystander effect (5) | + | + |
| Dependence on tissue oxygenation (5) | + | - |
| Dependence on cell cycle phase (5) | + | - |

Figure 9

SEQUENCE LISTING

```
<160> NUMBER OF SEQ ID NOS: 4

<210> SEQ ID NO 1
<211> LENGTH: 1952
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tctagaccac catggagaaa gacacactcc tgctatgggt cctacttctc tgggttccag      60
gttccacagg tgacattcag atgacccagt ctccgagctc tctgtccgca tcagtaggag     120
acagggtcac catcacatgc agagccagcg aaagtgtcga caattatggc attagcttta     180
tgaactggtt ccaacagaaa cccgggaagg ctcctaagct tctgatttac gctgcatcca     240
accaaggctc cggggtaccc tctcgcttct caggcagtgg atctgggaca gacttcactc     300
```

```
tcaccatttc atctctgcag cctgatgact tcgcaaccta ttactgtcag caaagtaagg    360
aggttccgtg gacgttcggt caagggacca aggtggagat caaacgtaag tagaatccaa    420
agtctagaaa ttctaaactc tgaggggtc ggatgacgtg gccattcttt gcctaaagca     480
ttgagtttac tgcaaggtca gaaaagcatg caaagccctc agaatggctg caagagctc     540
caacaaaaca atttagaact ttattaagga ataggggaa gctaggaaga aactcaaaac     600
atcaagattt taaatacgct tcttggtctc cttgctataa ttatctggga taagcatgct    660
gttttctgtc tgtccctaac atgctctgtg attatccgca acaacacac ccaagggcag     720
aactttgtta cttaaacacc atcctgtttg cttctttcct caggaactgt ggctgcacca    780
tctgtcttca tcttcccgcc atctgatgag cagttgaaat ctggaactgc ctctgttgtg    840
tgcctgctga ataacttcta tcccagagag gccaaagtac agtggaaggt ggataacgcc    900
ctccaatcgg gtaactccca ggagagtgtc acagagcagg acagcaagga cagcacctac    960
agcctcagca gcaccctgac gctgagcaaa gcagactacg agaaacacaa agtctacgcc   1020
tgcgaagtca cccatcaggg cctgagctcg cccgtcacaa agagcttcaa caggggagag   1080
tgttagaggg agaagtgccc ccacctgctc ctcagttcca gcctgacccc ctcccatcct   1140
ttggcctctg acccttttc cacaggggac ctacccctat gcggtcctc cagctcatct    1200
ttcacctcac cccctcctc ctccttggct ttaattatgc taatgttgga ggagaatgaa   1260
taaataaagt gaatctttgc acctgtggtt tctctctttc ctcatttaat aattattatc   1320
tgttgtttta ccaactactc aatttctctt ataagggact aaatatgtag tcatcctaag   1380
gcgcataacc atttataaaa atcatccttc attctatttt accctatcat cctctgcaag   1440
acagtcctcc ctcaaaccca caagccttct gtcctcacag tccctgggc catggtagga   1500
gagacttgct tccttgtttt cccctcctca gcaagccctc atagtccttt ttaagggtga   1560
caggtcttac agtcatatat cctttgattc aattccctga gaatcaacca agcaaattt    1620
ttcaaaagaa gaaacctgct ataaagagaa tcattcattg caacatgata taaaataaca   1680
acacaataaa agcaattaaa taaacaaaca atagggaaat gtttaagttc atcatggtac   1740
ttagacttaa tggaatgtca tgccttattt acatttttaa acaggtactg agggactcct   1800
gtctgccaag ggccgtattg agtactttcc acaacctaat ttaatccaca ctatactgtg   1860
agattaaaaa cattcattaa aatgttgcaa aggttctata aagctgagag acaaatatat   1920
tctataactc agcaatccca cttctaggat cc                                 1952
```

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Lys Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Ser
        35                  40                  45

Val Asp Asn Tyr Gly Ile Ser Phe Met Asn Trp Phe Gln Gln Lys Pro
    50                  55                  60

Gly Lys Ala Pro Lys Leu Leu Ile Tyr Ala Ala Ser Asn Gln Gly Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Asp Asp Phe Ala Thr Tyr Tyr Cys
            100                 105                 110

Gln Gln Ser Lys Glu Val Pro Trp Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 3
<211> LENGTH: 3246
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tctagaccac catgggatgg agctggatct ttctcttcct cctgtcagga actgctggcg      60
tccactctca ggttcagctg gtgcagtctg gagctgaggt gaagaagcct gggagctcag     120
tgaaggtttc ctgcaaagct tctggctaca ccttcactga ctacaacatg cactgggtga     180
ggcaggctcc tggccaaggc ctggaatgga ttggatatat ttatccttac aatggtggta     240
ccggctacaa ccagaagttc aagagcaagg ccacaattac agcagacgag agtactaaca     300
cagcctacat ggaactctcc agcctgaggt ctgaggacac tgcagtctat tactgcgcaa     360
gagggcgccc cgctatggac tactggggcc aagggactct ggtcactgtc tcttcaggta     420
agaatggcct ctagaccacc atgggatgga gctttctggg gcaggccagg cctgaccttg     480 gctttgggc agggaggggg ctaaggtgag gcaggtggcg ccagccaggt gcacacccaa     540
tgcccatgag cccagacact ggacgctgaa cctcgcggac agttaagaac caggggcct     600 ctgcgccctg ggcccagctc tgtcccacac cgcggtcaca tggcaccacc tctcttgcag     660
cctccaccaa gggcccatcg gtcttccccc tggcaccctc ctccaagagc acctctgggg     720
gcacagcggc cctgggctgc ctggtcaagg actacttccc cgaaccggtg acggtgtcgt     780
ggaactcagg cgccctgacc agcggcgtgc acaccttccc ggctgtccta cagtcctcag     840
gactctactc cctcagcagc gtggtgaccg tgccctccag cagcttgggc acccagacct     900
acatctgcaa cgtgaatcac aagcccagca acaccaaggt ggacaagaaa gttggtgaga     960
ggccagcaca gggagggagg gtgtctgctg gaagccaggc tcagcgctcc tgcctggacg    1020

```
catcccggct atgcagcccc agtccagggc agcaaggcag gccccgtctg cctcttcacc    1080
cggaggcctc tgcccgcccc actcatgctc agggagaggg tcttctggct ttttccccag    1140
gctctgggca ggcacaggct aggtgcccct aacccaggcc ctgcacacaa aggggcaggt    1200
gctgggctca gacctgccaa gagccatatc cggaggacc ctgcccctga cctaagccca    1260
ccccaaaggc caaactctcc actccctcag ctcggacacc ttctctcctc ccagattcca    1320
gtaactccca atcttctctc tgcagagccc aaatcttgtg acaaaactca cacatgccca    1380
ccgtgcccag gtaagccagc ccaggcctcg ccctccagct caaggcggga caggtgccct    1440
agagtagcct gcatccaggg acaggcccca gccgggtgct gacacgtcca cctccatctc    1500
ttcctcagca cctgaactcc tggggggacc gtcagtcttc ctcttccccc caaaacccaa    1560
ggacaccctc atgatctccc ggaccctga ggtcacatgc gtggtggtgg acgtgagcca    1620
cgaagaccct gaggtcaagt tcaactggta cgtggacggc gtggaggtgc ataatgccaa    1680
gacaaagccg cggaggagc agtacaacag cacgtaccgt gtggtcagcg tcctcaccgt    1740
cctgcaccag gactggctga atggcaagga gtacaagtgc aaggtctcca acaaagccct    1800
cccagccccc atcgagaaaa ccatctccaa agccaaaggt gggacccgtg gggtgcgagg    1860
gccacatgga cagaggccgg ctcggcccac cctctgccct gagagtgacc gctgtaccaa    1920
cctctgtccc tacagggcag ccccgagaac acaggtgta cccctgccc catcccggg    1980 atgagctgac caagaaccag gtcagcctga cctgcctggt caaaggcttc tatcccagcg    2040
acatcgccgt ggagtgggag agcaatgggc agccggagaa caactacaag accacgcctc    2100
ccgtgctgga ctccgacggc tccttcttcc tctacagcaa gctcaccgtg gacaagagca    2160
ggtggcagca ggggaacgtc ttctcatgct ccgtgatgca tgaggctctg cacaaccact    2220
acacgcagaa gagcctctcc ctgtctccgg gtaaatgagt gcgacggccg gcaagccccc    2280
gctccccggg ctctcgcggt cgcacgagga tgcttggcac gtacccctg tacatacttc    2340 ccgggcgccc agcatggaaa taaagcaccc agcgctgccc tgggccctg cgagactgtg    2400 atggttcttt ccacgggtca ggccgagtct gaggcctgag tggcatgagg gaggcagagc    2460
gggtcccact gtccccacac tggcccaggc tgtgcaggtg tgcctgggcc gcctagggtg    2520
gggctcagcc aggggctgcc ctcggcaggg tgggggattt gccagcgtgg ccctccctcc    2580
agcagcacct gccctgggct gggcacggg aagccctagg agcccctggg acagacaca    2640 cagcccctgc ctctgtagga gactgtcctg ttctgtgagc gccctgtcct ccgacctcca    2700
tgcccactcg ggggcatgcc tagtccatgt gcgtagggac aggccctccc tcacccatct    2760 accccacgg cactaacccc tggctgccct gcccagcctc gcacccgcat ggggacacaa    2820
ccgactccgg ggacatgcac tctcgggccc tgtggaggga ctggtgcaga tgcccacaca    2880
cacactcagc ccagacccgt tcaacaaacc ccgcactgag gttggccggc cacacggcca    2940
ccacacacac acgtgcacgc ctcacacacg gagcctcacc cggcgaact gcacagcacc    3000 cagaccagag caaggtcctc gcacacgtga acactcctcg gacacaggcc cccacgagcc    3060
ccacgcggca cctcaaggcc cacgagcctc tcggcagctt ctccacatgc tgacctgctc    3120
agacaaaccc agccctcctc tcacaagggt gcccctgcag ccgccacaca cacacagggg    3180
atcacacacc acgtcacgtc cctggccctg gcccacttcc cagtgccgcc cttccctgca    3240
ggatcc                                                              3246
```

<210> SEQ ID NO 4
<211> LENGTH: 465

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Gly Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asn Met His Trp Val Arg Gln Ala Pro Gly Gln Gly Leu
    50                  55                  60

Glu Trp Ile Gly Tyr Ile Tyr Pro Tyr Asn Gly Gly Thr Gly Tyr Asn
65                  70                  75                  80

Gln Lys Phe Lys Ser Lys Ala Thr Ile Thr Ala Asp Glu Ser Thr Asn
                85                  90                  95

Thr Ala Tyr Met Glu Leu Ser Ser Leu Arg Ser Glu Asp Thr Ala Val
            100                 105                 110

Tyr Tyr Cys Ala Arg Gly Arg Pro Ala Met Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380
```

-continued

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

METHOD FOR TREATING CANCER USING A BCL-2 INHIBITOR IN CONJUNCTION WITH AN ALPHA-EMITTING RADIOIMMUNOTHERAPEUTIC

This application is a § 371 national stage entry of PCT Application No. PCT/US2018/029607, filed Apr. 26, 2018, which claims the benefit of U.S. Provisional Application No. 62/491,803, filed Apr. 28, 2017, the contents of which are incorporated herein by reference.

The instant application contains a Sequence Listing that has been submitted electronically in ASCII format and is hereby incorporated by reference in its entirety. Said ASCII copy, created on Aug. 12, 2020, is named Actinium-5PUS-_SL.txt and is 13,870 bytes in size.

Throughout this application, various publications are cited. The disclosure of these publications is hereby incorporated by reference into this application to describe more fully the state of the art to which this invention pertains.

FIELD OF THE INVENTION

The present invention relates to treating a subject afflicted with cancer using a therapeutically effective regimen of a BCL-2 inhibitor in conjunction with an alpha-emitting isotope-labeled agent that targets cancer cells in the subject.

BACKGROUND OF THE INVENTION

BCL-2 Inhibitors

BCL-2 inhibitors have potential for treating malignancies. One such BCL-2 inhibitor is venetoclax, a drug that has been approved for treating chronic lymphocytic leukemia ("CLL") (1). Venetoclax binds to the BH3-binding groove of BCL-2, displacing pro-apoptotic proteins like BIM to initiate mitochondrial outer membrane permeabilization ("MOMP"), the release of cytochrome c, and caspase activation, ultimately resulting in programmed cancer cell death (i.e., apoptosis) (2).

Apoptosis is a mechanism of cell death in cancer cells, in addition to necrosis and autophagy (3). Ideally, by changing the balance between pro-apoptotic and anti-apoptotic stimuli, venetoclax would facilitate programed cell death of cancer cells and thus improve cancer patient outcomes.

However, apoptosis is a complex pathway. Cancer cells can develop various mechanisms to circumvent and/or abrogate a given treatment strategy intended to cause apoptotic death (4) (as presented in FIG. 1 of that reference). For example, X-linked XIAP can abrogate the blocking of BCL-2. XIAP is a well-characterized inhibitor of apoptosis proteins (IAPs) (5). Indeed, the majority of human cancers harbor high levels of IAPs such as XIAP (6).

Other possible mechanisms of circumventing the effect of BCL-2 inhibitors can be seen in FIG. 7. These include blocking activation of caspase 8 to prevent the downstream activity of venetoclax on the BAX/BCL-2 axis. Also, stimulating or un-blocking one part of the apoptotic pathway may not be sufficient to cause apoptosis, as pro-apoptotic stimuli are still needed to trigger an apoptotic pathway (7), (8).

Consequently, not all cancer cells respond to BCL-2 inhibitors. In one venetoclax trial, for example, the complete response rate (including complete responses with incomplete marrow recovery) was 7.5%, even though a majority of patients (79.4%) had some level of response to venetoclax (2). In addition, venetoclax has a significant myelosuppressive effect on neutrophils, with 40% of patients experiencing grade 3 and/or 4 neutropenia (2).

Radiation

Radiation is a recognized way to treat cancer. It is known that cellular effects of radiation include cell cycle arrest, mutation, apoptosis, necrosis and autophagy (9). Radiation-related mediators of cellular damage include: (i) direct LED (linear energy deposition); (ii) ROS (reactive oxygen species); and (iii) RNS (reactive nitrogen species) (9).

These mediators lead to cell damage/kill/arrest via the following mechanisms: (i) DNA damage (9) (e.g., double-strand DNA breaks (most efficient), single-strand DNA breaks (less efficient, repairable), DNA base damage (least efficient, repairable), and DNA crosslinks); (ii) direct effects on the apoptotic cascade (e.g., direct activation of caspases, and damage to IAPs) (10); and (iii) bystander effects (i.e., damage or killing of cells not directly damaged by radiation, which damage or killing occurs through mediation via gap junction communication and/or cytokines from target cells) (11).

The Unpredictability of Combination Therapies

In a mouse xenograft model of venetoclax and radiation synergy (12), mice treated with a combination of venetoclax and $^{90}$Y-based radioimmunotherapy had better survival rates compared to mice treated with either venetoclax or the radioimmunotherapy alone. Survival outcomes in xenografted mouse cohorts are shown in FIG. 8.

Importantly, however, these mouse results may not be applicable to humans. Indeed, there are various factors that could render infeasible the treatment of cancer in humans using radiation in conjunction with venetoclax.

One such factor is oxygenation. Xenografted mice had small tumor masses in Fred Hutchinson Cancer Research Center experiments. Diffuse large B-cell lymphoma ("DLBCL") tumor xenografts were treated at a volume of 50 mm$^3$, implying a tumor diameter of under 0.5 cm. For DLBCL patients in an MD Anderson study, ~25% of patients had tumor diameters greater than 7 cm (13). In large xenografted tumors in rats, it was found that in tumors larger than 3.5 cm$^3$, baseline hypoxia was greater than 80%, while tumors smaller than 2.5 cm$^3$ had baseline hypoxia of ~20% (14). Hypoxia confers resistance to irradiation by lowering the creation of ROS (15), (16), (17). High tumor burden with hypoxic areas in human disease would significantly abrogate beta radiation-induced ROS and RNS.

Another such factor is the range of feasible dose levels. In mouse experiments on candidate therapeutics, the mice typically receive doses of drug weight per body weight that cannot be applied to humans. For example, in the $^{90}$Y/venetoclax combination experiment described above, mice were treated with doses of 800 µCi and 1,200 µCi per mouse (whereby 800 µCi was used in combination with venetoclax). Eight hundred µCi in a mouse would correspond to 3,000 mCi in an average human. By comparison, Zevalin® ($^{90}$Y-RIT, ibritumomab tiuxetan) can be administered to patients at a dose not exceeding 32 mCi (18).

There remains a need for a cancer therapy that solves the problems seen with BCL-2 inhibitors such as venetoclax and radiation therapies such as $^{90}$Y-based therapies.

SUMMARY OF THE INVENTION

This invention provides a method for treating a subject afflicted with cancer, comprising administering to the subject (i) a BCL-2 inhibitor in conjunction with (ii) an alpha-emitting isotope-labeled agent that targets cancer cells in the subject, wherein the amounts of the BCL-2 inhibitor and labeled agent, when administered in conjunction with one another, are therapeutically effective.

This invention also provides a method for treating a human subject afflicted with acute myeloid leukemia, comprising administering to the subject (i) venetoclax in conjunction with (ii) $^{225}$Ac-labeled HuM195, wherein the amounts of venetoclax and $^{225}$Ac-labeled HuM195, when administered in conjunction with one another, are therapeutically effective.

This invention further provides a method for inducing the death of a cancer cell, comprising contacting the cell with (i) a BCL-2 inhibitor in conjunction with (ii) an alpha-emitting isotope-labeled agent that targets the cancer cell, wherein the amounts of BCL-2 inhibitor and labeled agent, when concurrently contacted with the cell, are effective to induce the cell's death.

Finally, this invention also provides a method for inducing the death of an acute myeloid leukemic cell, comprising contacting the cell with (i) venetoclax in conjunction with (ii) $^{225}$Ac-labeled HuM195, wherein the amounts of venetoclax and $^{225}$Ac-labeled HuM195, when concurrently contacted with the cell, are effective to induce the cell's death.

Figure 1:
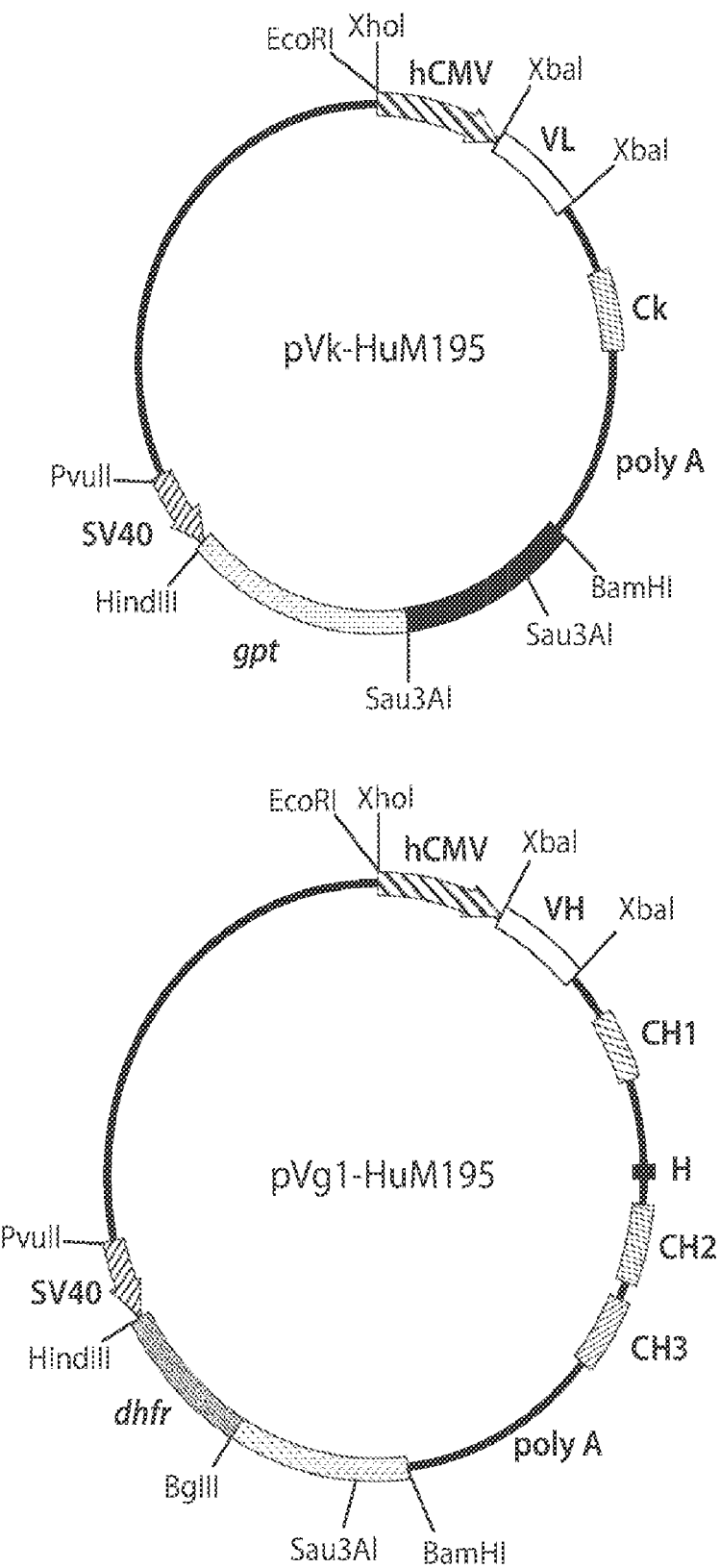
FIG. 1

This figure shows a schematic diagram of the expression plasmids for HuM195. The humanized VL and VH exons of HuM195 are flanked by XbaI sites. The VL exon was inserted into mammalian expression vector pVk, and the VH exon into pVg1 (Co, et al., J. Immunol. 148:1149-1154, 1992).

FIG. 2

This figure shows the complete sequence of the HuM195 light chain gene cloned in pVk between the XbaI and BamHI sites. The nucleotide number indicates its position in the plasmid pVk-HuM195. The VL and CK exons are translated in single letter code; the dot indicates the translation termination codon. The mature light chain begins at the double-underlined aspartic acid (D). The intron sequence is in italics. The polyA signal is underlined.

FIG. 3

This figure shows the complete sequence of the HuM195 heavy chain gene cloned in pVg1 between the XbaI and BamHI sites. The nucleotide number indicates its position in the plasmid pVg1-HuM195. The VH, CH1, H, CH2 and CH3 exons are translated in single letter code; the dot indicates the translation termination codon. The mature heavy chain begins at the double-underlined glutamine (Q). The intron sequences are in italics. The polyA signal is underlined.

FIG. 4

This figure shows the structure of $^{225}$Ac-Lintuzumab ($^{225}$Ac-HuM195).

FIG. 5

This figure shows a flowchart for the production of $^{225}$Ac-HuM195.

FIG. 6

This figure shows a dosing protocol for $^{225}$Ac-Lintuzumab ($^{225}$Ac-HuM195) treatment of AML.

FIG. 7

This figure shows a schematic of apoptotic cell death and mechanisms of cancer cells resistance to apoptosis (modified from (4)).

FIG. 8

This figure shows a diagram of survival of xenografted mice treated with venetoclax alone, targeted beta radioimmunotherapy alone, and a combination of venetoclax and targeted beta radioimmunotherapy. In Rec-1-bearing mice, venetoclax had no effect alone (p=0.12), 800 μCi PRIT lengthened survival time 111% beyond controls (p=0.0001), while the combination extended survival 483% beyond controls and cured 40% (p=0.001, combination group>PRIT alone). In the U2932 xenograft model, venetoclax alone doubled survival time compared to controls (p<0.0001) and 800 μCi PRIT alone doubled survival and cured 30%. Combination treatments cured 100% (12).

FIG. 9

This figure shows a comparison between beta and alpha radiation mechanisms of apoptotic cell killing. As the figure shows, alpha radiation is significantly more potent than beta radiation (~700 times); causes more dsDNA breaks than beta radiation; does not depend on tissue oxygenation and the cell division phase; and can overcome cellular resistance to beta and gamma radiation and cytotoxic chemotherapy. These findings are collectively supported by (9)-(11) and (22)-(24).

DETAILED DESCRIPTION OF THE INVENTION

This invention provides methods for treating a subject afflicted with cancer. These methods comprise administering to the subject two types of agents in conjunction with one another. The first type of agent is a BCL-2 inhibitor such as venetoclax. The second type is an alpha-emitting isotope-labeled agent, such as $^{225}$Ac-labeled HuM195, that targets cancer cells in the subject.

Definitions

In this application, certain terms are used which shall have the meanings set forth as follows.

As used herein, "administer", with respect to an agent, means to deliver the agent to a subject's body via any known method. Specific modes of administration include, without limitation, intravenous, oral, sublingual, transdermal, subcutaneous, intraperitoneal, intrathecal and intra-tumoral administration.

In addition, in this invention, the various antibodies and other antigen-targeting agents used can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

As used herein, the term "agent", whether in reference to a BCL-2 inhibitor or an alpha-emitting isotope-labeled agent, can be any type of compound or composition useful for such purpose. Types of agents include, without limitation, antibodies, other protein-based drugs, peptides, nucleic acids, carbohydrates and small molecules drugs.

As used herein, the term "alpha-emitting isotope" includes, without limitation, $^{225}$Ac, $^{213}$Bi and $^{213}$Po. Methods for affixing an alpha-emitting isotope to an antibody (i.e., "labeling" an antibody with an alpha-emitting isotope) are well known.

As used herein, the term "antibody" includes, without limitation, (a) an immunoglobulin molecule comprising two heavy chains and two light chains and which recognizes an antigen; (b) polyclonal and monoclonal immunoglobulin molecules; (c) monovalent and divalent fragments thereof, and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human, humanized or nonhuman.

As used herein, an "anti-CD33 antibody" is an antibody that binds to any available epitope of CD33. In one embodiment, the anti-CD33 antibody binds to the epitope recognized by the antibody HuM195.

As used herein, the term "burden", when used in connection with a cancerous cell, means quantity. So, a cancerous cell "burden" means the quantity of cancerous cells. Cancerous cells have a burden with respect to their tissue of origin (i.e., the primary site of disease), such as the "bone marrow blast burden" in the case of AML. Cancerous cells also have a burden with respect to one or more tissues other than those of origin, such as the blast burden in blood, liver and spleen in the case of AML. The term "peripheral burden" relates to such cells. The peripheral burden of cancerous cells, such as blasts in the case of AML, can be measured in different ways with different outcomes. For example, in the case of AML, the "peripheral blast burden" can be measured as the total blast population outside of the bone marrow, or the total blast population of the blood, spleen and liver combined, or simply the blast population of the blood as measured in cells per unit volume. As used herein in connection with AML and other cancers originating in the bone marrow, and unless stated otherwise, the term "peripheral cancerous cell burden" (e.g., peripheral blast burden) refers to the cancerous cell population of the blood as measured in cells per unit volume (e.g., cells/µl). This blood-based measurement is a useful proxy for the more cumbersome measurements of spleen and liver burdens, for example.

Herein, a peripheral cancerous cell burden in a subject is "high" if, when the subject is administered an agent (e.g., an antibody) targeting a hematologic malignancy-associated antigen at the maximum safe dose, the agent does not reach the primary site of disease in a sufficient amount to bind to more than 90% of its target antigens at that site. Conversely, a peripheral cancerous cell burden in a subject is "low" if, when the subject is administered an agent (e.g., an antibody) targeting a hematologic malignancy-associated antigen at the maximum safe dose, the agent reaches the primary site of disease in a sufficient amount to bind to more than 90% of its target antigens at that site. In the case of AML, examples of low peripheral blast burden are those yielding blood blast burdens at or below 1,000 blast cells/µl, at or below 500 blast cells/µl, at or below 400 blast cells/µl, at or below 300 blast cells/µl, at or below 200 blast cells/µl, at or below 100 blast cells/µl, and at or below 50 blast cells/µl.

A "hematologic malignancy", also known as a blood cancer, is a cancer that originates in blood-forming tissue, such as the bone marrow or other cells of the immune system. Hematologic malignancies include, without limitation, leukemias (such as AML, acute promyelocytic leukemia, acute lymphoblastic leukemia, acute mixed lineage leukemia, chronic myeloid leukemia, chronic lymphocytic leukemia, hairy cell leukemia and large granular lymphocytic leukemia), myelodysplastic syndrome (MDS), myeloproliferative disorders (polycythemia vera, essential thrombocytosis, primary myelofibrosis and chronic myeloid leukemia), lymphomas, multiple myeloma, and MGUS and similar disorders.

As used herein, a "hematologic malignancy-associated antigen" can be, for example, a protein and/or carbohydrate marker found exclusively or predominantly on the surface of a cancer cell associated with that particular malignancy. Examples of hematologic malignancy-associated antigens include, without limitation, CD20, CD33, CD38, CD45, CD52, CD123 and CD319.

The antibody "HuM195" (also known as lintuzumab) is known, as are methods of making it. Likewise, methods of labeling HuM195 with $^{225}$Ac are known. These methods are exemplified, for example, in Scheinberg, et al., U.S. Pat. No. 6,683,162. This information is also exemplified in the examples and figures below.

As used herein, administering to a subject a BCL-2 inhibitor "in conjunction with" an alpha-emitting isotope-labeled agent that targets cancer cells in the subject means administering the BCL-2 inhibitor before, during or after administration of the labeled agent. This administration includes, without limitation, the following scenarios: (i) the BCL-2 inhibitor is administered first (e.g., orally once per day for 21 days, 28 days, 35 days, 42 days, 49 days, or a longer period during which the cancer being treated does not progress and during which the BCL-2 inhibitor does not cause unacceptable toxicity), and the labeled agent is administered second (e.g., intravenously in a single dose or a plurality of doses over a period of weeks); (ii) the BCL-2 inhibitor is administered concurrently with the labeled agent (e.g., the BCL-2 inhibitor is administered orally once per day for n days, and the labeled agent is administered intravenously in a single dose on one of days 2 through n−1 of the BCL-2 inhibitor regimen); (iii) the BCL-2 inhibitor is administered concurrently with the labeled agent (e.g., the BCL-2 inhibitor is administered orally for a duration of greater than one month (e.g., orally once per day for 35 days, 42 days, 49 days, or a longer period during which the cancer being treated does not progress and during which the BCL-2 inhibitor does not cause unacceptable toxicity), and the labeled agent is administered intravenously in a single dose on a day within the first month of the BCL-2 inhibitor regimen); and (iv) the labeled agent is administered first (e.g., intravenously in a single dose or a plurality of doses over a period of weeks), and the BCL-2 inhibitor is administered second (e.g., orally once per day for 21 days, 28 days, 35 days, 42 days, 49 days, or a longer period during which the cancer being treated does not progress and during which the BCL-2 inhibitor does not cause unacceptable toxicity). Additional permutations are provided below in the Examples section.

As used herein, the term "subject" includes, without limitation, a mammal such as a human, a non-human primate, a dog, a cat, a horse, a sheep, a goat, a cow, a rabbit, a pig, a rat and a mouse. Where the subject is human, the subject can be of any age. For example, the subject can be 60 years or older, 65 or older, 70 or older, 75 or older, 80 or older, 85 or older, or 90 or older. Alternatively, the subject can be 50 years or younger, 45 or younger, 40 or younger, 35 or younger, 30 or younger, 25 or younger, or 20 or younger. For a human subject afflicted with AML, the subject can be newly diagnosed, or relapsed and/or refractory, or in remission.

As used herein, a "sub-saturating dose" of an agent targeting an antigen (e.g., CD33) or marker (e.g., BCL-2) is one that introduces into the subject's body fewer target antigen-binding sites (e.g., Fab's) than there are target antigens, or fewer target marker-binding sites (e.g., venetoclax molecules) than there are target markers, as applicable. By way of example, for an anti-CD33 antibody, a sub-saturating dose is one that introduces into the subject's body fewer CD33-binding sites than there are CD33 molecules. In one embodiment, a sub-saturating dose of an agent targeting a hematologic malignancy-associated antigen is one where the ratio of target antigen-binding sites to target antigens is less than or equal to 9:10. In another embodiment, the ratio of target antigen-binding sites to target antigens is less than or equal to 1:2, less than or equal to 1:5, less than or equal to 1:10, less than or equal to 1:20, or less than or equal to 1:100. By way of additional example, for a BCL-2 inhibitor, a sub-saturating dose is one that introduces into the subject's body fewer BCL-2-binding sites than there are BCL-2 proteins. In one embodiment, a sub-saturating dose of a BCL-2 inhibitor is one where the ratio of inhibitor to BCL-2 protein is less than or equal to 9:10. In another embodiment, the ratio of target antigen-binding sites to target antigens is less than or equal to 1:2, less than or equal to 1:5, less than or equal to 1:10, less than or equal to 1:20, or less than or equal to 1:100. In a further embodiment, a "sub-saturating dose" of a BCL-2 inhibitor (e.g., venetoclax) is a dose lower than the inhibitor's maximum approved dose in humans (e.g., below 400 mg per day, below 300 mg per day, below 200 mg per day, below 100 mg per day, below 50 mg per day, or below 10 mg per day).

For an agent such as an antibody labeled with an alpha-emitting isotope, the majority of the drug administered to a subject typically consists of non-labeled antibody, with the minority being the labeled antibody. Thus, in one embodiment, a sub-saturating dose of an agent targeting a hematologic malignancy-associated antigen is one where the ratio of total (i.e., labeled and unlabeled) target antigen-binding sites to target antigens is less than or equal to 9:10 (and can be less than or equal to 1:2, less than or equal to 1:5, less than or equal to 1:10, less than or equal to 1:20, or less than or equal to 1:100). In another embodiment, a sub-saturating dose of an agent targeting a hematologic malignancy-associated antigen is one where the ratio of labeled target antigen-binding sites to target antigens is less than or equal to 9:10 (and can be less than or equal to 1:2, less than or equal to 1:5, less than or equal to 1:10, less than or equal to 1:20, or less than or equal to 1:100).

Sub-saturating doses of labeled agent used in connection with this invention include, for example, a single administration, and two or more administrations (i.e., fractions). The amount administered in each dose can be measured, for example, by labeled radiation activity (e.g., µCi/kg) or antibody weight (e.g., µg/kg or µg/m$^2$). In the case of $^{225}$Ac-HuM195 for treating AML, human dosing regimens include the following, without limitation: (i) 2×<0.5 µCi/kg, 2×0.5 µCi/kg, 2×1.0 µCi/kg, 2×1.5 µCi/kg, or 2×2.0 µCi/kg, where the fractions are administered one week apart; (ii) <0.5 µCi/kg, or from 0.5 µCi/kg to 10 µCi/kg; (iii) 2×<7.5 µg/kg, 2×7.5 µg/kg, 2×10 µg/kg, or 2×12.5 µg/kg, where the fractions are administered one week apart; or (iv) <15 µg/kg, or from 15 µg/kg to 50 µg/kg.

As used herein, an amount of BCL-2 inhibitor and an amount of alpha-emitting isotope-labeled agent that targets cancer cells in the subject, when administered in conjunction with each other, are "therapeutically effective" if the subject is treated.

As used herein, "treating" a subject afflicted with a disorder shall include, without limitation, (i) slowing, stopping or reversing the disorder's progression, (ii) slowing, stopping or reversing the progression of the disorder's symptoms, (iii) reducing the likelihood of the disorder's recurrence, and/or (iv) reducing the likelihood that the disorder's symptoms will recur. In the preferred embodiment, treating a subject afflicted with a disorder means (i) reversing the disorder's progression, ideally to the point of eliminating the disorder, and/or (ii) reversing the progression of the disorder's symptoms, ideally to the point of eliminating the symptoms, and/or (iii) reducing or eliminating the likelihood of relapse (i.e., consolidation, which is a common goal of post-remission therapy for AML and, ideally, results in the destruction of any remaining leukemia cells).

The treatment of hematologic malignancy, such as the treatment of AML, can be measured according to a number of clinical endpoints. These include, without limitation, survival time (such as weeks, months or years of improved survival time, e.g., one, two or more months' of additional survival time), and response status (such as complete remission (CR), complete remission with incomplete platelet recovery (CRp), complete remission with incomplete peripheral blood recovery (CRi), morphologic leukemia-free state (MLFS) and partial remission (PR)).

In one embodiment, treatment of hematologic malignancy, such as the treatment of AML, can be measured in terms of remission. Included here are the following non-limiting examples. (1) Morphologic complete remission ("CR"): ANC≥1,000/mcl, platelet count≥100,000/mcl, <5% bone marrow blasts, no Auer rods, no evidence of extramedullary disease. (No requirements for marrow cellularity, hemoglobin concentration). (2) Morphologic complete remission with incomplete blood count recovery ("CRi"): Same as CR but ANC may be <1,000/mcl and/or platelet count<100,000/mcl. (3) Partial remission (PR): ANC≥1,000/mcl, platelet count>100,000/mcl, and at least a 50% decrease in the percentage of marrow aspirate blasts to 5-25%, or marrow blasts<5% with persistent Auer rods. These criteria and others are known, and are described, for example, in SWOG Oncology Research Professional (ORP) Manual Volume I, Chapter 11A, Leukemia (2014).

Embodiments of the Invention

This invention employs the use of alpha particles. These particles induce apoptosis in target cells, e.g., leukemic cells (10), (19). Alpha-emitters and beta-emitters induce apoptosis with different efficiencies at comparable activities in leukemic cells (10). Alpha particles can overcome doxorubicin-resistance, CD95-resistance, and radio-resistance to beta-irradiation and gamma-irradiation in leukemic cells (10). The particles induce apoptosis via: (i) double-strand DNA breaks (20), (21); (ii) activation of caspases; (iii) the fact that [$^{213}$Bi]anti-CD45 activates caspases 2, 3, 8 and 9 through the mitochondrial pathway independent of the CD95 ligand/receptor system (10), (19); and (iv) inactivation of XIAP and Bcl-XL (19).

Specifically, this invention provides a first therapeutic method. This first method is for treating a subject afflicted with cancer, comprising administering to the subject (i) a BCL-2 inhibitor in conjunction with (ii) an alpha-emitting isotope-labeled agent that targets cancer cells in the subject, wherein the amounts of the BCL-2 inhibitor and labeled agent, when administered in conjunction with one another, are therapeutically effective.

This invention also provides a second therapeutic method. This second method is for treating a human subject afflicted with acute myeloid leukemia, comprising administering to the subject (i) venetoclax in conjunction with (ii) $^{225}$Ac-labeled HuM195, wherein the amounts of venetoclax and $^{225}$Ac-labeled HuM195, when administered in conjunction with one another, are therapeutically effective.

Preferably in the first and second therapeutic methods, the subject is human. In one embodiment of the first and second therapeutic methods, the cancer is a hematologic malignancy, and preferably is a leukemia such as acute myeloid leukemia.

In the preferred embodiment of the first and second therapeutic methods, the BCL-2 inhibitor is venetoclax. Also in the preferred embodiment of the first and second therapeutic methods, the alpha-emitting isotope-labeled agent is an anti-CD33 antibody labeled with an alpha-emitting isotope, ideally $^{225}$Ac-labeled HuM195. In these methods, the BCL-2 inhibitor, the labeled agent, or both, are preferably administered (i) in sub-saturating doses, and/or (ii) in doses that are less than (and/or shorter duration than) those presently prescribed on their respective labels. Also in these methods, the subject's peripheral blast burden is preferably low, and the methods preferably do not cause unacceptable levels of neutropenia.

This invention provides a third method. This third method is for inducing the death of a cancer cell, comprising contacting the cell with (i) a BCL-2 inhibitor in conjunction with (ii) an alpha-emitting isotope-labeled agent that targets the cancer cell, wherein the amounts of BCL-2 inhibitor and labeled agent, when concurrently contacted with the cell, are effective to induce the cell's death.

Preferably, the cancer cell is a human cancer cell. In one embodiment, the cancer cell is a hematologic cell, and preferably is a leukemic cell such as an acute myeloid leukemic cell.

In the preferred embodiment, the BCL-2 inhibitor is venetoclax. Also in the preferred embodiment, the alpha-emitting isotope-labeled agent is an anti-CD33 antibody labeled with an alpha-emitting isotope, ideally $^{225}$Ac-labeled HuM195.

This invention also provides a fourth method. This fourth method is for inducing the death of an acute myeloid leukemic cell, comprising contacting the cell with (i) venetoclax in conjunction with (ii) $^{225}$Ac-labeled HuM195, wherein the amounts of venetoclax and $^{225}$Ac-labeled HuM195, when concurrently contacted with the cell, are effective to induce the cell's death.

Finally, this invention provides two articles of manufacture. The first article comprises (i) a BCL-2 inhibitor (e.g., venetoclax) and (ii) a label instructing the user (e.g., the patient or healthcare provider) to treat a subject afflicted with cancer (e.g., acute myeloid leukemia) by administering the BCL-2 inhibitor to the subject in conjunction with an alpha-emitting isotope-labeled agent that targets cancer cells in the subject (e.g., $^{225}$Ac-labeled HuM195), wherein the amounts of the BCL-2 inhibitor and labeled agent, when administered in conjunction with one another, are therapeutically effective. The second article comprises (i) an alpha-emitting isotope-labeled agent that targets cancer cells (e.g., $^{225}$Ac-labeled HuM195) and (ii) a label instructing the user to treat a subject afflicted with cancer (e.g., acute myeloid leukemia) by administering the labeled agent to the subject in conjunction with a BCL-2 inhibitor (e.g., venetoclax), wherein the amounts of the BCL-2 inhibitor and labeled agent, when administered in conjunction with one another, are therapeutically effective.

Wherever applicable, the methods of the subject invention may also be performed using pre-targeted radioimmunotherapy (PRIT). A PRIT-based method comprises the steps of (i) administering a monoclonal antibody labeled with a marker (e.g., streptavidin), (ii) then administering a suitable clearing agent (e.g., a biotin galactose clearing agent), and (iii) administering an alpha-emitting isotope-labeled agent that specifically binds to the marker (e.g., $^{225}$Ac-labeled biotin). Therefore, the various embodiments of the invention relating to non-PRIT-based methods for administering an alpha-emitting isotope-labeled agent apply, mutatis mutandis, to these PRIT-based methods.

This invention will be better understood by reference to the examples which follow, but those skilled in the art will readily appreciate that the specific examples detailed are only illustrative of the invention as described more fully in the claims which follow thereafter.

EXAMPLES

Example 1—Structure of $^{225}$Ac-Lintuzumab ($^{225}$Ac-HuM195)

Figure 4:
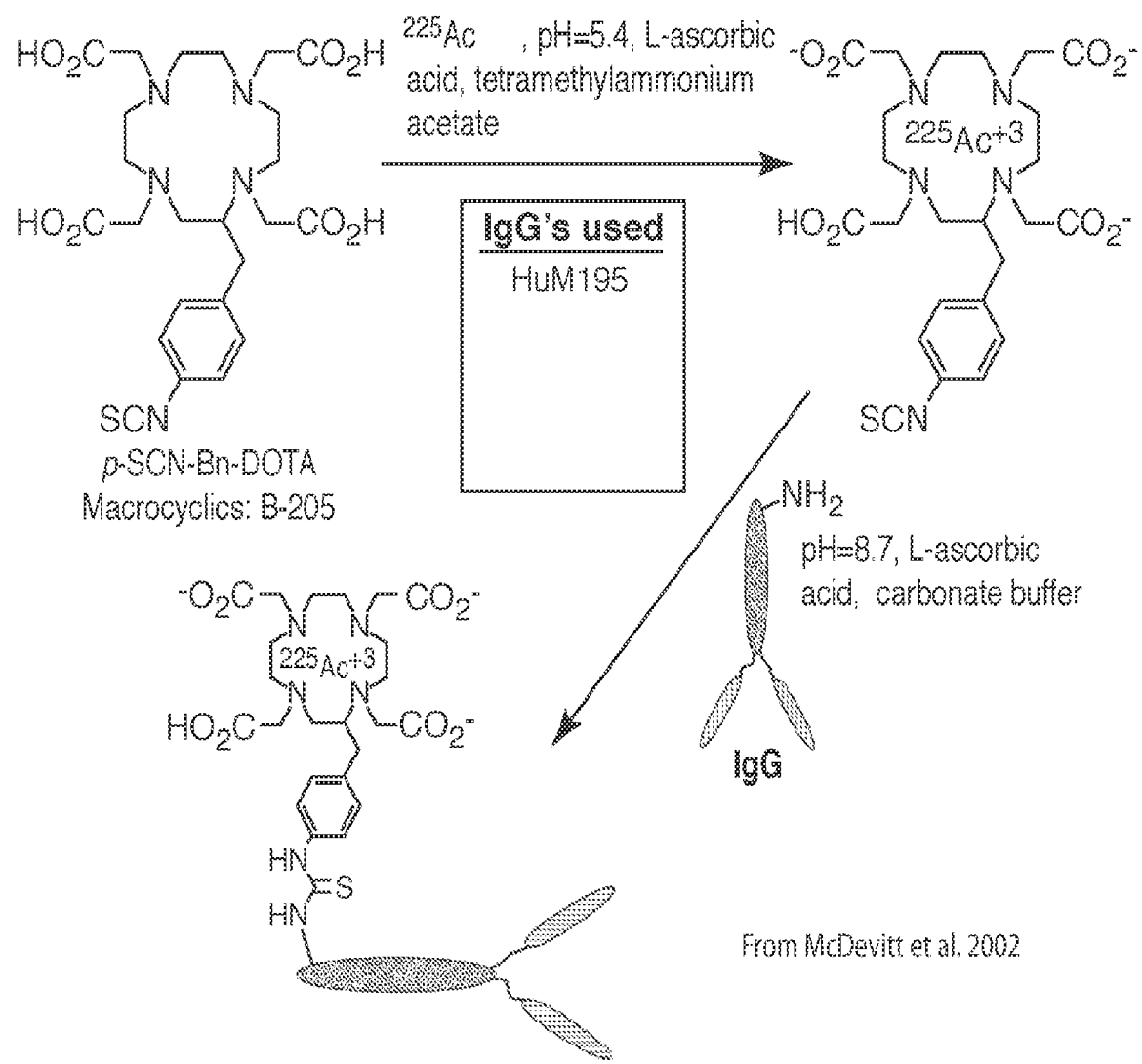

$^{225}$Ac-Lintuzumab includes three key components; humanized monoclonal antibody HuM195 (generic name, lintuzumab), the alpha-emitting radioisotope $^{225}$Ac, and the bi-functional chelate 2-(p-isothiocyanatobenzyl)-1,4,7,10-tetraazacyclododecane-1,4,7,10-tetraacetic acid (p-SCN-Bn-DOTA). As depicted in FIG. 4, HuM195 is radiolabeled using the bi-functional chelate p-SCN-Bn-DOTA that binds to $^{225}$Ac and that is covalently attached to the IgG via a lysine residue on the antibody.

Example 2—p-SCN-Bn-DOTA

DOTA, 2-(4-Isothiocyanatobenzyl)-1,4,7,10-tetraazacyclododecane tetraacetic acid (Macrocyclics item code B205-GMP) is synthesized by a multi-step organic synthesis that is fully described in U.S. Pat. No. 4,923,985.

Example 3—Preparation of $^{225}$Ac-Lintuzumab ($^{225}$Ac-HuM195)

The procedure for preparing $^{225}$Ac-Lintuzumab is based on the method described by Michael R. McDevitt, "Design and synthesis of $^{225}$Ac radioimmuno-pharmaceuticals, Applied Radiation and Isotope", 57 (2002), 841-847. The procedure involves radiolabeling the bi-functional chelate, p-SCN-Bn-DOTA, with the radioisotope $^{225}$Ac, followed by binding of the radiolabeled p-SCN-Bn-DOTA to the antibody (HuM195). The construct, $^{225}$Ac-p-SCN-Bn-DOTA-HuM195, is purified using 10 DG size exclusion chromatography and eluted with 1% human serum albumin (HSA). The resulting drug product, Ac$^{225}$-Lintuzumab, is then passed through a 0.2 μm sterilizing filter.

Example 4—Process Flow for Preparation of $^{225}$Ac-Lintuzumab ($^{225}$Ac-HuM195)

Figure 5:
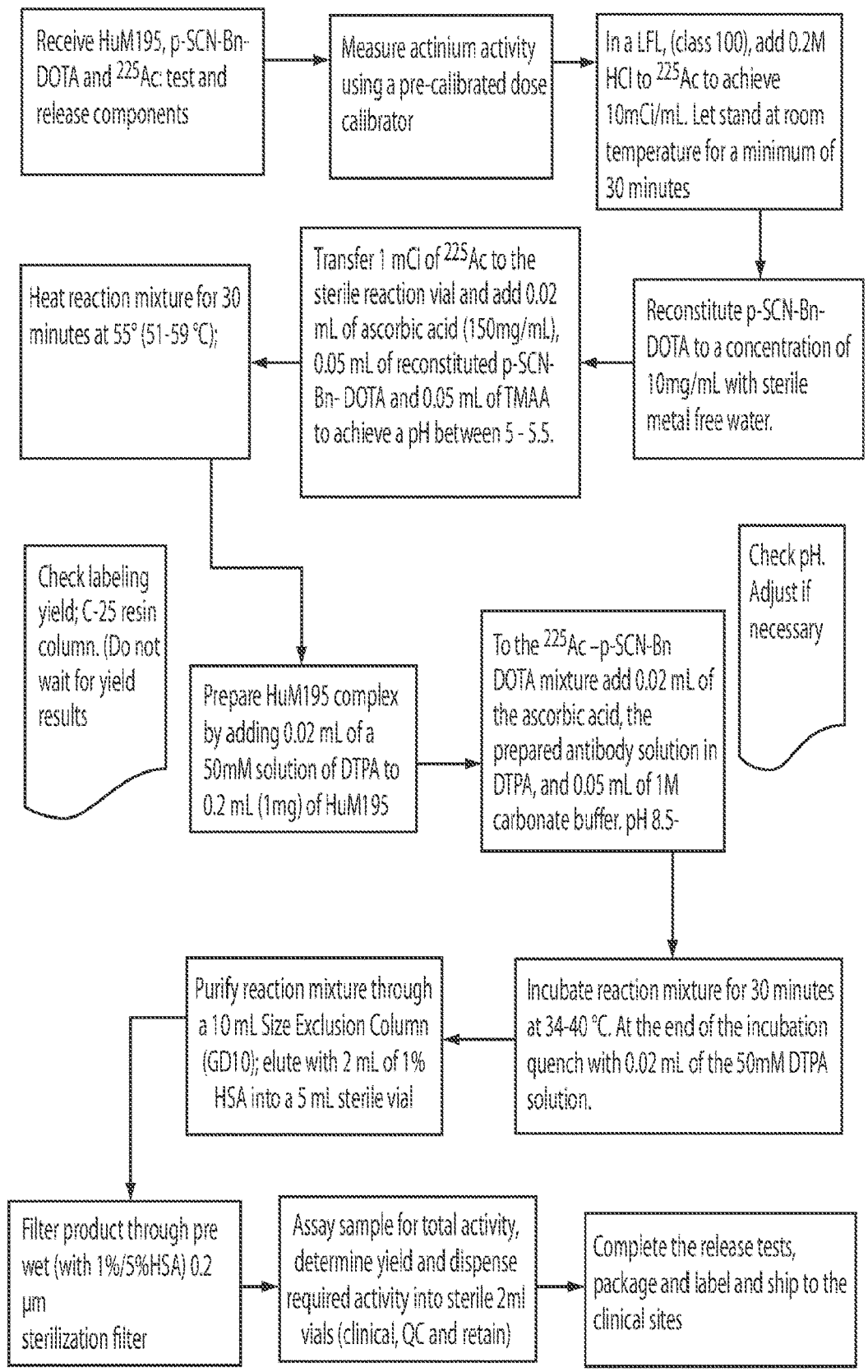
Figure 7:
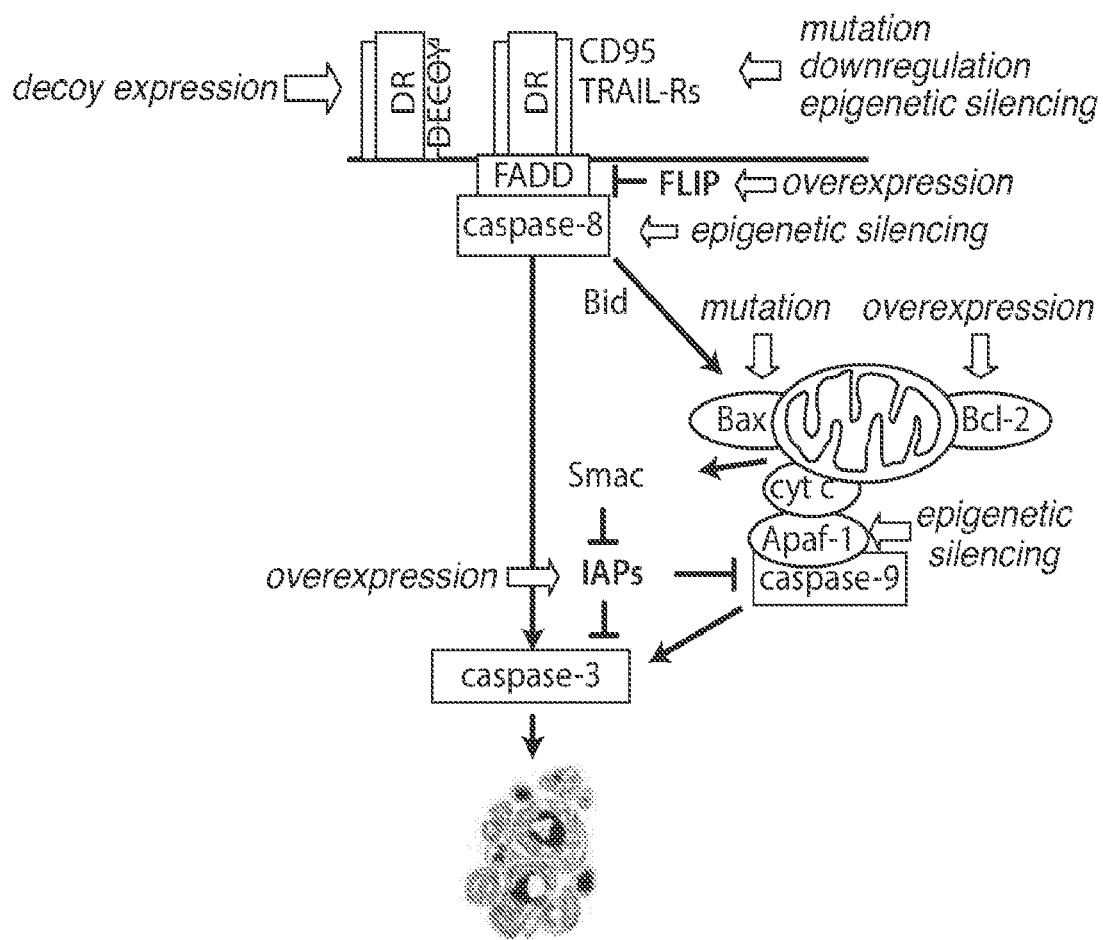
Figure 8:
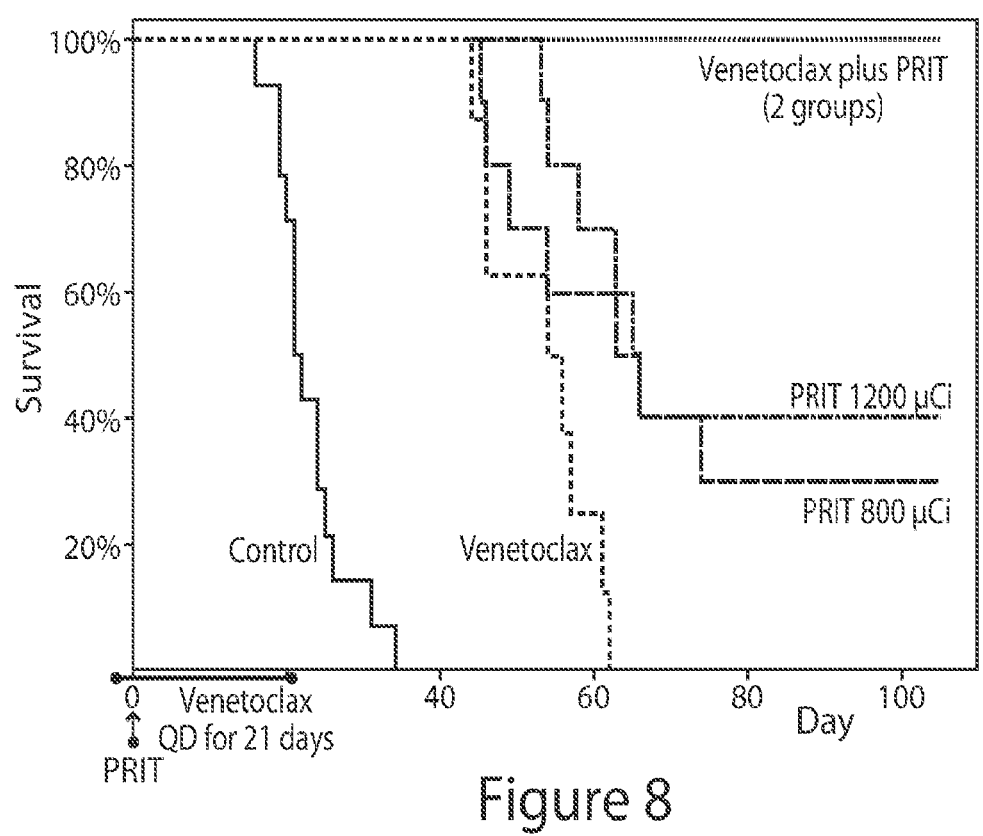

The procedure, shown in FIG. 5, begins with confirming the identity of all components and the subsequent QC release of the components to production. The $^{225}$Ac is assayed to confirm the level of activity and is reconstituted to the desired activity concentration with hydrochloric acid. A vial of lyophilized p-SCN-Bn-DOTA is reconstituted with metal-free water to a concentration of 10 mg/mL. To the actinium reaction vial, 0.02 ml of ascorbic acid solution (150 mg/mL) and 0.05 ml of reconstituted p-SCN-Bn-DOTA are added and the pH adjusted to between 5 and 5.5 with 2M tetramethylammonium acetate (TMAA). The mixture is then heated at 55±4° C. for 30 minutes.

To determine the labeling efficiency of the $^{225}$Ac-p-SCN-Bn-DOTA, an aliquot of the reaction mixture is removed and applied to a 1 ml column of Sephadex C25 cation exchange resin. The product is eluted in 2-4 ml fractions with a 0.9% saline solution. The fraction of $^{225}$Ac activity that elutes is $^{225}$Ac-p-SCN-Bn-DOTA and the fraction that is retained on the column is un-chelated, unreactive $^{225}$Ac. Typically, the labeling efficiency is greater than 95%.

To the reaction mixture, 0.22 ml of previously prepared HuM195 in DTPA (1 mg HuM195) and 0.02 ml of ascorbic acid are added. The DTPA is added to bind any trace amounts of metals that may compete with the labeling of the antibody. The ascorbic acid is added as a radio-protectant. The pH is adjusted with carbonate buffer to pH 8.5-9. The mixture is heated at 37±3° C. for 30 minutes.

The final product is purified by size exclusion chromatography using 10DG resin and eluted with 2 ml of 1% HSA. Typical reaction yields are 10%.

Example 5—Venetoclax and its Normal Dosing Regimen

Venetoclax is sold by Genentech (San Francisco, Calif.) under the brand name Venclexta™. According to the FDA's Venclexta™ label, this drug "is a BCL-2 inhibitor indicated for the treatment of patients with chronic lymphocytic leukemia (CLL) with 17p deletion . . . who have received at least one prior therapy." Venclexta™ is sold in tablet form at 10 mg, 50 mg and 100 mg. Therapy is to be initiated "at 20 mg once daily for 7 days, followed by a weekly ramp-up dosing schedule to the recommended daily dose of 400 mg." The ramp-up dosing schedule is as follows: week 1, 20 mg/day; week 2, 50 mg/day; week 3, 100 mg/day; week 4, 200 mg/day; and week 5 and beyond, 400 mg/day. This dosing regimen is referred to herein as the "normal" human dosing regimen for venetoclax, regardless of the disorder treated. Any dosing regimen having a shorter duration (e.g., 21 days) or involving the administration of less venetoclax (e.g., 20 mg/day for a total of 21 days) is referred to herein as a "reduced" human dosing regimen. The terms "normal" human dosing regimen and "reduced" human dosing regimen also apply, mutatis mutandis, to any other BCL-2 inhibitor with respect to its approved or otherwise customary dosing regimen.

Also envisioned is a "normal" murine dosing regimen and a "reduced" murine dosing regimen, each being commensurate with mouse body weight and tumor xenograft size. Moreover, the "normal" murine dosing regimen has a duration of at least 21 days.

Example 6—$^{225}$Ac-HuM195 and its Normal Dosing Regimen

In the case of $^{225}$Ac-HuM195, the "normal" human dosing regimen (regardless of the disorder treated), as this term is used herein, includes either of the following: (i) 2×2.0 µCi/kg, where the fractions are administered one week apart; and (ii) 4.0 µCi/kg when delivered in a single administration. Any dosing regimen involving the administration of less $^{225}$Ac-HuM195 (e.g., 2.0 µCi/kg when delivered in a single administration) is referred to herein as a "reduced" human dosing regimen (which may also be considered a sub-saturating dose). The terms "normal" human dosing regimen and "reduced" human dosing regimen also apply, mutatis mutandis, to any other alpha-emitting isotope-labeled agent with respect to its approved or otherwise customary dosing regimen.

Also envisioned is a "normal" murine dosing regimen and a "reduced" murine dosing regimen, each being commensurate with mouse body weight and tumor xenograft size.

Example 7—Dosing Scenario I for $^{225}$Ac-HuM195 and Venetoclax

A human AML patient is treated according to the following regimen. Venetoclax is orally administered according to its normal dosing regimen (i.e., for at least five weeks), followed by intravenous administration of $^{225}$Ac-HuM195 according to its normal dosing regimen (either single or fractional administration). In one embodiment, the first (and only, if applicable) dose of $^{225}$Ac-HuM195 is administered on the same day as, or one day following, the last dose of venetoclax.

Also envisioned is the treatment of an experimental mouse model according to the treatment regimen in this scenario, whereby the appropriate dosing regimens are commensurate with mouse body weight and tumor xenograft size.

Example 8—Dosing Scenario II for $^{225}$Ac-HuM195 and Venetoclax

A human AML patient is treated according to the following regimen. Venetoclax is orally administered according to its normal dosing regimen (i.e., for at least five weeks), followed by intravenous administration of a reduced dosing regimen of $^{225}$Ac-HuM195 (either single or fractional administration). In one embodiment, the first (and only, if applicable) dose of $^{225}$Ac-HuM195 is administered on the same day as, or one day following, the last dose of venetoclax. In another embodiment, the reduced dosing regimen of $^{225}$Ac-HuM195 is (i) 2×0.5 µCi/kg, 2×1.0 µCi/kg, or 2×1.5 µCi/kg, where the fractions are administered one week apart; or (ii) 1×0.5 µCi/kg, 1×1.0 µCi/kg, 1×2.0 µCi/kg, or 1×3.0 µCi/kg, for a single administration.

Also envisioned is the treatment of an experimental mouse model according to the treatment regimen in this scenario, whereby the appropriate dosing regimens are commensurate with mouse body weight and tumor xenograft size.

Example 9—Dosing Scenario III for $^{225}$Ac-HuM195 and Venetoclax

A human AML patient is treated according to the following regimen. Venetoclax is orally administered according to a reduced dosing regimen, followed by intravenous administration of the normal dosing regimen of $^{225}$Ac-HuM195 (either single or fractional administration). In one embodiment, the first (and only, if applicable) dose of $^{225}$Ac-HuM195 is administered on the same day as, or one day following, the last dose of venetoclax. In another embodiment, the reduced dosing regimen of venetoclax is one of the following: (i) 20 mg once daily for 7 days; (ii) 20 mg once daily for 14 days; (iii) 20 mg once daily for 21 days; (iv) 50 mg once daily for 7 days; (v) 50 mg once daily for 14 days; (vi) 50 mg once daily for 21 days; (vii) 100 mg once daily for 7 days; (viii) 100 mg once daily for 14 days; (ix) 100 mg once daily for 21 days; (x) 200 mg once daily for 7 days; (xi) 200 mg once daily for 14 days; (xii) 200 mg once daily for 21 days; (xiii) 400 mg once daily for 7 days; and (xiv) week 1 at 20 mg/day, week 2 at 50 mg/day and week 3 at 100 mg/day.

Also envisioned is the treatment of an experimental mouse model according to the treatment regimen in this scenario, whereby the appropriate dosing regimens are commensurate with mouse body weight and tumor xenograft size.

Example 10—Dosing Scenario IV for $^{225}$Ac-HuM195 and Venetoclax

A human AML patient is treated according to the following regimen. Venetoclax is orally administered according to a reduced dosing regimen, followed by intravenous administration of a reduced dosing regimen of $^{225}$Ac-HuM195 (either single or fractional administration). In one embodiment, the first (and only, if applicable) dose of $^{225}$Ac-HuM195 is administered on the same day as, or one day following, the last dose of venetoclax. In another embodiment, (a) the reduced dosing regimen of venetoclax is one of (i) 20 mg once daily for 7 days; (ii) 20 mg once daily for 14 days; (iii) 20 mg once daily for 21 days; (iv) 50 mg once daily for 7 days; (v) 50 mg once daily for 14 days; (vi) 50 mg once daily for 21 days; (vii) 100 mg once daily for 7 days; (viii) 100 mg once daily for 14 days; (ix) 100 mg once daily for 21 days; (x) 200 mg once daily for 7 days; (xi) 200 mg once daily for 14 days; (xii) 200 mg once daily for 21 days; (xiii) 400 mg once daily for 7 days; and (xiv) week 1 at 20 mg/day, week 2 at 50 mg/day and week 3 at 100 mg/day; and (b) the reduced dosing regimen of $^{225}$Ac-HuM195 is one of (i) 2×0.5 µCi/kg, 2×1.0 µCi/kg, or 2×1.5 µCi/kg, where the fractions are administered one week apart; or (ii) 1×0.5 µCi/kg, 1×1.0 µCi/kg, 1×2.0 µCi/kg, or 1×3.0 µCi/kg, for a single administration.

Also envisioned is the treatment of an experimental mouse model according to the treatment regimen in this scenario, whereby the appropriate dosing regimens are commensurate with mouse body weight and tumor xenograft size.

Example 11—Dosing Scenario V for $^{225}$Ac-HuM195 and Venetoclax

A human AML patient is treated according to the following regimen. Venetoclax is orally administered according to its normal dosing regimen (i.e., for at least five weeks), and $^{225}$Ac-HuM195 is intravenously administered according to its normal single dose regimen during the course of the venetoclax dosing regimen. In one embodiment, the single dose of $^{225}$Ac-HuM195 is administered (a) on day 1, 2, 3, 4, 5, 6, 7, 8, 9, 10, 11, 12, 13, 14, 15, 16, 17, 18, 19, 20 or 21 of the venetoclax dosing regimen, or (b) on the last day of, the penultimate day of, or 2, 3, 4, 5, 6, 7, 8, 9, 10, 11, 12, 13, 14, 15, 16, 17, 18, 19, 20 or 21 days prior to the last day of, the venetoclax dosing regimen.

Also envisioned is the treatment of an experimental mouse model according to the treatment regimen in this scenario, whereby the appropriate dosing regimens are commensurate with mouse body weight and tumor xenograft size.

Example 12—Dosing Scenario VI for $^{225}$Ac-HuM195 and Venetoclax

A human AML patient is treated according to the following regimen. Venetoclax is orally administered according to its normal dosing regimen (i.e., for at least five weeks), and $^{225}$Ac-HuM195 is intravenously administered according to a reduced single dose regimen during the course of the venetoclax dosing regimen. In one embodiment, the single dose of $^{225}$Ac-HuM195 is administered (a) on day 1, 2, 3, 4, 5, 6, 7, 8, 9, 10, 11, 12, 13, 14, 15, 16, 17, 18, 19, 20 or 21 of the venetoclax dosing regimen, or (b) on the last day of, the penultimate day of, or 2, 3, 4, 5, 6, 7, 8, 9, 10, 11, 12, 13, 14, 15, 16, 17, 18, 19, 20 or 21 days prior to the last day of, the venetoclax dosing regimen. In another embodiment, the reduced dosing regimen of $^{225}$Ac-HuM195 is (i) 2×0.5 µCi/kg, 2×1.0 µCi/kg, or 2×1.5 µCi/kg, where the fractions are administered one week apart; or (ii) 1×0.5 µCi/kg, 1×1.0 µCi/kg, 1×2.0 µCi/kg, or 1×3.0 µCi/kg, for a single administration.

Also envisioned is the treatment of an experimental mouse model according to the treatment regimen in this scenario, whereby the appropriate dosing regimens are commensurate with mouse body weight and tumor xenograft size.

Example 13—Dosing Scenario VII for $^{225}$Ac-HuM195 and Venetoclax

A human AML patient is treated according to the following regimen. Venetoclax is orally administered according to a reduced dosing regimen, and $^{225}$Ac-HuM195 is intravenously administered according to its normal single dose regimen during the course of the venetoclax dosing regimen. In one embodiment, the single dose of $^{225}$Ac-HuM195 is administered (a) on day 1, 2, 3, 4, 5, 6, 7, 8, 9, 10, 11, 12, 13, 14, 15, 16, 17, 18, 19, 20 or 21 of the venetoclax dosing regimen, or (b) on the last day of, the penultimate day of, or 2, 3, 4, 5, 6, 7, 8, 9, 10, 11, 12, 13, 14, 15, 16, 17, 18, 19, 20 or 21 days prior to the last day of, the venetoclax dosing regimen. In another embodiment, the reduced dosing regimen of venetoclax is one of the following: (i) 20 mg once daily for 7 days; (ii) 20 mg once daily for 14 days; (iii) 20 mg once daily for 21 days; (iv) 50 mg once daily for 7 days; (v) 50 mg once daily for 14 days; (vi) 50 mg once daily for 21 days; (vii) 100 mg once daily for 7 days; (viii) 100 mg once daily for 14 days; (ix) 100 mg once daily for 21 days; (x) 200 mg once daily for 7 days; (xi) 200 mg once daily for 14 days; (xii) 200 mg once daily for 21 days; (xiii) 400 mg once daily for 7 days; and (xiv) week 1 at 20 mg/day, week 2 at 50 mg/day and week 3 at 100 mg/day.

Also envisioned is the treatment of an experimental mouse model according to the treatment regimen in this scenario, whereby the appropriate dosing regimens are commensurate with mouse body weight and tumor xenograft size.

Example 14—Dosing Scenario VIII for $^{225}$Ac-HuM195 and Venetoclax

A human AML patient is treated according to the following regimen. Venetoclax is orally administered according to a reduced dosing regimen, and $^{225}$Ac-HuM195 is intravenously administered according to a reduced single dose regimen during the course of the venetoclax dosing regimen. In one embodiment, the single dose of $^{225}$Ac-HuM195 is administered (a) on day 1, 2, 3, 4, 5, 6, 7, 8, 9, 10, 11, 12, 13, 14, 15, 16, 17, 18, 19, 20 or 21 of the venetoclax dosing regimen, or (b) on the last day of, the penultimate day of, or 2, 3, 4, 5, 6, 7, 8, 9, 10, 11, 12, 13, 14, 15, 16, 17, 18, 19, 20 or 21 days prior to the last day of, the venetoclax dosing regimen. In another embodiment, (a) the reduced dosing regimen of venetoclax is one of (i) 20 mg once daily for 7 days; (ii) 20 mg once daily for 14 days; (iii) 20 mg once daily for 21 days; (iv) 50 mg once daily for 7 days; (v) 50 mg once daily for 14 days; (vi) 50 mg once daily for 21 days; (vii) 100 mg once daily for 7 days; (viii) 100 mg once daily for 14 days; (ix) 100 mg once daily for 21 days; (x) 200 mg once daily for 7 days; (xi) 200 mg once daily for 14 days; (xii) 200 mg once daily for 21 days; (xiii) 400 mg once daily for 7 days; and (xiv) week 1 at 20 mg/day, week 2 at 50 mg/day and week 3 at 100 mg/day; and (b) the reduced dosing regimen of $^{225}$Ac-HuM195 is one of (i) 2×0.5 µCi/kg, 2×1.0 µCi/kg, or 2×1.5 µCi/kg, where the fractions are administered one week apart; or (ii) 1×0.5 µCi/kg, 1×1.0 µCi/kg, 1×2.0 µCi/kg, or 1×3.0 µCi/kg, for a single administration.

Also envisioned is the treatment of an experimental mouse model according to the treatment regimen in this scenario, whereby the appropriate dosing regimens are commensurate with mouse body weight and tumor xenograft size.

REFERENCES

1. FDA News Release, FDA approves new drug for chronic lymphocytic leukemia in patients with a specific chromosomal abnormality, Apr. 11, 2016.
2. Venclexta™ Product Monograph Including Patient Medication Information (2016).
3. G. Kroemer, et al., Classification of Cell Death: Recommendations of the Nomenclature Committee on Cell Death 2009. Cell Death and Differentiation (2009) 16, 3-11.
4. S. Fulda, Tumor resistance to apoptosis, Int. J. Cancer: 124, 511-515 (2009).
5. E. Shiozaki, et al., Mechanism of XIAP-Mediated Inhibition of Caspase-9. Molecular Cell, Vol. 11, 519-527, February 2003.
6. I. Tamm, et al., Expression and prognostic significance of IAP-family genes in human cancers and myeloid leukemias. Clin Cancer Res. 2000; 6(5):1796-1803.
7. D. Potter and A. Letai, To Prime, or Not to Prime: That Is the Question, Cold Spring Harbor Symposia on Quantitative Biology, Volume LXXXI, Nov. 3, 2016.
8. Venetoclax Advisory Committee Briefing Document, Jun. 28, 2016.
9. J. Kiang, et al., Radiation Combined Injury: DNA Damage, Apoptosis, and Autophagy. Adaptive Medicine 2(1): 1-10, 2010.
10. C. Friesen, et al., Breaking Chemoresistance and Radioresistance with [$^{213}$Bi]anti-CD45 Antibodies in Leukemia Cells, Cancer Res 2007, 67(5):1950-8.
11. S. Sofou, Radionuclide carriers for targeting of cancer, International Journal of Nanomedicine 2008:3(2), 181-199.
12. S. O'Steen, et al., Venetoclax Synergizes with Radiation Therapy for Treatment of B-Cell Lymphomas, ASH Annual Meeting 2016, Abstract 467.
13. R. Wilder, et al., International Prognostic Index-Based Outcomes for Diffuse Large B-Cell Lymphomas. CANCER Jun. 15, 2002/Volume 94/Number 12.
14. V. Bourke, et al., Correlation of Radiation Response with Tumor Oxygenation in the Dunning Prostate R3327-AT1 Tumor. Int. J. Radiat. Oncol. Biol. Phys. 2007 Mar. 15; 67(4):1179-1186.
15. P. Vaupel, Tumor microenvironmental physiology and its implications for radiation oncology. Seminars in Radiation Oncology, Vol. 14, Issue 3, July 2004.
16. L. Harrison, et al., Hypoxia and Anemia: Factors in Decreased Sensitivity to Radiation Therapy and Chemotherapy? The Oncologist 2004, 9 (Suppl. 5), 31-40.
17. M. Hockel, et al., Tumor Hypoxia: Definitions and Current Clinical, Biologic, and Molecular Aspects, Journal of the National Cancer Institute, Vol. 93, No. 4, Feb. 21, 2001.
18. Zevalin® U.S.A. Package Insert (2001).
19. M. Roscher, et al., Targeted alpha-therapy using [Bi-213]anti-CD20 as novel treatment option for radio- and chemoresistant non-Hodgkin lymphoma cells, Oncotarget, February 2013, Vol. 4, No 2.
20. A. Konishi, et al., Involvement of Histone H1.2 in Apoptosis Induced by DNA Double-Strand Breaks. Cell, Vol. 114, 673-688, Sep. 19, 2003.
21. J. Stap, et al., Induction of linear tracks of DNA double-strand breaks by alpha-particle irradiation of cells. Nat. Methods, 2008 March, 5(3):261-6. doi: 10.1038/nmeth.f.206.
22. Pogozelski, et al., Quantitative assessment of the contribution of clustered damage to DNA double-strand breaks induced by 60Co gamma rays and fission neutrons. Radiat. Res. 1999 April, 151(4):442-8.
23. F. Graf, et al., (2014), DNA Double Strand Breaks as Predictor of Efficacy of the Alpha-Particle Emitter Ac-225 and the Electron Emitter Lu-177 for Somatostatin Receptor Targeted Radiotherapy. PLoS ONE 9(2): e88239. doi:10.1371/journal.pone.0088239.
24. P. A. Jeggo and M. Lobrich, DNA double-strand breaks: their cellular and clinical impact? Oncogene (2007) 26, 7717-7719.

What is claimed is:

1. A method for treating a mammalian subject afflicted with acute myeloid leukemia, consisting essentially of administering to the subject (i) a BCL-2 inhibitor in conjunction with (ii) an anti-CD33 antibody labeled with an alpha-emitting isotope, wherein (i) and (ii) when administered in conjunction with one another are therapeutically effective.

2. The method of claim 1, wherein the subject is human.

3. The method of claim 2, wherein the BCL-2 inhibitor is venetoclax.

4. The method of claim 3, wherein the acute myeloid leukemia is relapsed and/or refractory.

5. The method of claim 2, wherein the acute myeloid leukemia is relapsed and/or refractory.

6. The method of claim 1, wherein the BCL-2 inhibitor is venetoclax.

7. The method of claim 1, wherein the anti-CD33 antibody labeled with an alpha-emitting isotope is 225Ac-labeled HuM195.

8. The method of claim 2, wherein the anti-CD33 antibody labeled with an alpha-emitting isotope is 225Ac-labeled HuM195.

9. A method for treating a human subject afflicted with acute myeloid leukemia, consisting essentially of administering to the subject (i) venetoclax in conjunction with (ii) 225Ac-labeled HuM195, wherein the amounts of venetoclax and 225Ac-labeled HuM195, when administered in conjunction with one another, are therapeutically effective.

10. A method for inducing the death of an acute myeloid leukemia cell, consisting essentially of contacting the cell with (i) a BCL-2 inhibitor in conjunction with (ii) an anti-CD33 antibody labeled with an alpha-emitting isotope, wherein the amounts of BCL-2 inhibitor and the anti-CD33 antibody labeled with an alpha-emitting isotope, when concurrently contacted with the cell, are effective to induce the cell's death.

11. The method of claim 10, wherein the cancer cell is a human acute myeloid leukemia cell.

12. The method of claim 10, wherein the BCL-2 inhibitor is venetoclax.

13. The method of claim 10, wherein the anti-CD33 antibody labeled with an alpha-emitting isotope is 225Ac-labeled HuM195.

14. A method for inducing the death of an acute myeloid leukemic cell, consisting essentially of contacting the cell with (i) venetoclax in conjunction with (ii) 225Ac-labeled HuM195, wherein the amounts of venetoclax and 225Ac-labeled HuM195, when concurrently contacted with the cell, are effective to induce the cell's death.

15. The method of claim 1, wherein the alpha-emitting isotope is 225Ac.

16. The method of claim 1, wherein the anti-CD33 antibody labeled with an alpha-emitting isotope is HuM195 labeled with an alpha-emitting isotope.

17. The method of claim 9, wherein the acute myeloid leukemia is relapsed and/or refractory.

18. The method of claim 14, wherein the acute myeloid leukemia cell is a human acute myeloid leukemia cell.

* * * * *